United States Patent
He et al.

(10) Patent No.: US 6,211,359 B1
(45) Date of Patent: Apr. 3, 2001

(54) TRIAZA-CRYPTAND AND METHOD OF DETERMINING AN ALKALI ION

(75) Inventors: Huarui He, Alpharetta; Mark Alan Mortellaro, Woodstock, both of GA (US); Marco Jean Pierre Leiner, Graz (AT)

(73) Assignee: AVL Medical Instruments, Schaffhausen (CH)

( * ) Notice: Subject to any disclaimer, the term of this patent is extended or adjusted under 35 U.S.C. 154(b) by 0 days.

(21) Appl. No.: 09/375,366

(22) Filed: Aug. 17, 1999

(51) Int. Cl.[7] .................. C07D 419/14; C07D 498/08; G01N 21/64; G01N 33/20

(52) U.S. Cl. .............. 540/469; 540/467; 540/468; 436/79; 436/172

(58) Field of Search .................. 540/467, 468, 540/469; 436/79, 172

(56) References Cited

U.S. PATENT DOCUMENTS

| | | | |
|---|---|---|---|
| 5,162,525 | 11/1992 | Masilamani et al. | 540/468 |
| 5,439,828 | 8/1995 | Masilamani et al. | 436/74 |
| 5,948,906 * | 9/1999 | Tsien et al. | 540/467 |
| 6,001,999 * | 12/1999 | Wolfbeis et al. | 540/468 |

FOREIGN PATENT DOCUMENTS

881488A2  12/1998 (WO) .

OTHER PUBLICATIONS

Joseph R. Lakowicz, Topics in Fluorescence Spectroscopy, vol. 4:Probe Design and Chemical Sensing, Plenum Press, New York & London (1994).
Frank Kastenholz, Inaugural Dissertation, University of Cologne, 1993, Fig. 32, p. 54.
DeSilva, Tetrahedron Letters, vol. 31, No. 36, pp. 5193–5196 (1990).
Lehn JM, Sauvage JP, Amer. Chem. Soc. 97, pp. 6700–6207, 1985.

* cited by examiner

Primary Examiner—Mukund J. Shah
Assistant Examiner—Pavanaram K Sripada
(74) Attorney, Agent, or Firm—Birch, Stewart, Kolasch & Birch, LLP

(57) ABSTRACT

The invention relates to a triaza-cryptand of the general Formula I

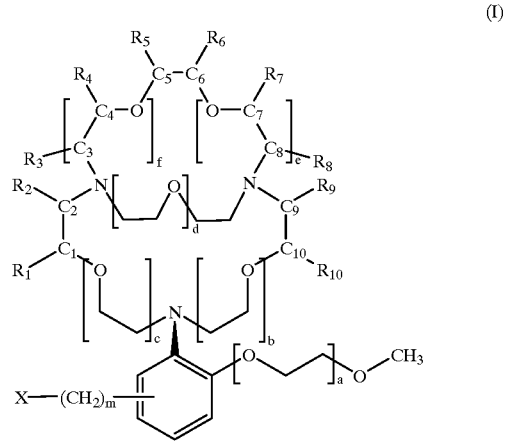

wherein a is selected from the group consisting of 0 and 1, b and c independently are selected from the group consisting of 0 and 1, with the proviso that not both of b and c are 0, d is selected from the group consisting of 1, 2 and 3, e and f independently are selected from the group consisting of 0 and 1, with the proviso that not both of e and f are 0, $R_1$ and $R_2$ are either hydrogen or form an alkyl($C_1$–$C_4$) benzene ring or an alkoxy($C_1C_4$) benzene ring together with $C_1$ and $C_2$, wherein $C_2$ is the para position, $R_3$ and $R_2$ are either hydrogen or form an alkyl($C_1$–$C_4$) benzene ring or an alkoxy($C_1$–$C_4$) benzene ring together with $C_3$ and $C_4$, wherein $C_3$ is the para position, $R_5$ and $R_6$ are either hydrogen or form a benzene ring or a naphtalene ring together with $C_5$ and $C_6$, $R_7$ and $R_8$ are either hydrogen or form an alkyl($C_1$–$C_4$) benzene ring or an alkoxy($C_1$–$C_4$) benzene ring together with $C_7$ and $C_8$, wherein $C_8$ is the para position, $R_9$ and $R_{10}$ are either hydrogen or form an alkyl($C_1$–$C_4$) benzene ring or an alkoxy($C_1$–$C_4$) benzene ring together with $C_9$ and $C_{10}$, wherein $C_9$ is the para position, X is a luminophoric moiety in ortho, para or meta position with respect to the nitrogen and m is selected from the group consisting of 0, 1 and 2.

The triaza-cryptand of the invention is useful as a luminescence indicator for alkali ions.

13 Claims, 20 Drawing Sheets

Q2  Q3  Q4  Q6

Q7  Q8  Q13  Q15

Q17  Q18  Q20  Q22  Q26

Q27  Q28  Q29  Q30

*All Aliphatic*

Q3      Q6      Q20      Q13

*Aliphatic/Aromatic*

Q4      Q8      Q26

*All Aromatic*

Q17      Q7      Q15

Q27      Q29      Q28

TRIAZA-CRYPTAND AND METHOD OF DETERMINING AN ALKALI ION

FIELD OF THE INVENTION

The invention relates to triaza-cryptands having a luminophoric moiety and an ionophoric moiety capable of being used as luminophore-ionophores (=indicators) for determining an alkali ion in a sample. The present invention also relates to a method of determining an alkali ion in a sample, wherein the alkali ion is contacted with the triaza-cryptand having a luminophoric moiety and an ionophoric moiety, which ionophoric moiety reversibly reacts with the alkali ion present in the sample, wherein the luminophoric moiety changes its luminescence properties, after which the luminescence is measured and the concentration or the activity of the alkali ion is deduced, i.e., the alkali ion is determined, utilizing the measured luminescence.

BACKGROUND OF THE INVENTION

A determination method of the type mentioned above is based on the reversible binding of cations to a cation-selective ionophore and the so-called "PET effect" between the ionophore and a luminophoric moiety.

The so-called "PET effect" denotes the transfer, induced by photons, of electrons (photoinduced electron transfer= PET) from the ionophoric moiety or ionophore, respectively, to the luminophoric moiety or luminophore, respectively, which leads to a decrease in the (relative) luminescence intensity and the luminescence decay time of the luminophore. Absorption and emission wavelengths, however, remain basically unaffected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect is partially or completely inhibited, so that there is an increase in the relative luminescence intensity and an increase in the luminescence decay time of the luminophoric moiety. Hence, the concentration or the activity of the ion to be determined can be deduced by measuring the luminescence properties, i.e., relative luminescence intensity and/or luminescence decay time. Activities can be related to concentrations via known Debye-Hückel formalisms.

It is known that cryptands preferably form complexes (cryptates) with such cations whose ion radius corresponds as well as possible to that of the cavity formed by the cryptand (Lehn J M, Sauvage J P, Amer. Chem. Soc. 97, 6700–6207, 1975). The ion diameters of the alkali metals Li, Na, K and Rb are 0.78, 0.98, 1.33 and 1.49 Angström, respectively. Thus, for a given cryptand the selectivity for a particular cation can be adjusted by changes in the ether chains. Furthermore, it is known that cryptands having indicator properties can be obtained by the coupling of cryptands to chromophores or luminophores.

A method of the kind initially described is known from U.S. Pat. No. 5,439,828, wherein diaza-cryptands are utilized as the luminophore-ionophore, which diaza-cryptands have been functionalized as fluorophores with fluorescent coumarins and, depending on their structure, are selective for lithium, sodium and potassium ions, respectively. It is stated that these luminophore-ionophores can be used in sample media of neutral pH and are even the preferred choice in such systems.

Yet, research (Frank Kastenholz, Inaugural Dissertation, University of Cologne, 1993, FIG. 32, p. 54) has shown that in the physiological pH range the fluorescence signal depends significantly on the pH of the sample and increases considerably with a decreasing pH, even from pH 7.4 onwards. This affects the accuracy of a determination carried out in a biological sample. Moreover, the compounds used have the additional disadvantage that the employed coumarins show absorption wavelengths of about 336 nm and hence cannot be excited by commercial LEDs.

These disadvantages also apply to the luminophore-ionophores mentioned in U.S. Pat. No. 5,162,525.

From DeSilva, Tetrahedron Letters, Volume 31, No. 36, pp. 5193–5196 (1990), diaza-cryptands are known in which the two nitrogen atoms are each bound to a respective aromatic ring, i.e., both bridging nitrogens are aryl nitrogens. Research conducted by the applicant has shown that these diaza-cryptands are not suited for determining potassium ions via a PET mechanims. By the binding of $K^+$ to these diaza-cryptands in the absence or in the presence of physiological $Na^+$ concentrations, the enhancement of the luminescence intensity of the fluorophore moiety (i.e., napthalimide) due to the PET effect is too small for a useful practical method.

From EP-A-0,881,488 diaza-cryptands are known in which one of the two bridging nitrogen atoms is an aryl nitrogen and the other one is an aliphatic nitrogen. From the perspective of synthesis, the production of those cryptands in quantities required for commercial use is expensive. EP-A-0,881,488 suggests the Williamson ether synthesis to make the precursors of the crown ether. The oily precursors are tedious to purify and the cyclization reactions give low yields. The overall yield of the synthetic path is low.

The present invention, therefore, has as its object to improve the known process and make available luminophore-ionophores which lack significant dependence of the luminescence properties on the pH value of the sample at physiological pH values and, thus, preferably are suitable for determining alkali ions in biological samples. In addition, the invention aims at providing luminophore-ionophores which are particularly well suited for use in the determination of $K^+$ ions in a sample. Further, the method of the invention is to be particularly well suited for practice in the determination of an alkali ion in the presence of physiological concentrations of other alkali ions, i.e., it should exhibit a strong dependence of the luminescent signal on the concentration of the alkali ion being determined.

BRIEF SUMMARY OF THE INVENTION

The object of the invention is achieved by providing as a luminophore-ionophore a triaza-cryptand of the general Formula I

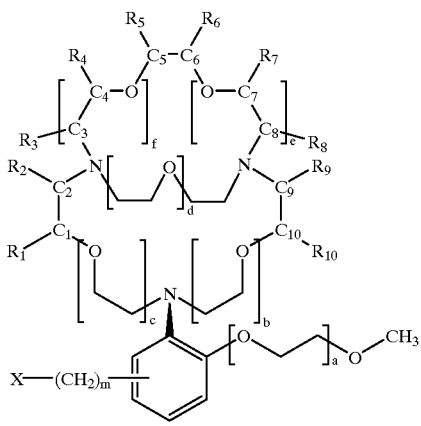

(I)

wherein
- a is selected from the group consisting of 0 and 1,
- b and c independently are selected from the group consisting of 0 and 1, with the proviso that not both of b and c are 0,
- d is selected from the group consisting of 1, 2 and 3,
- e and f independently are selected from the group consisting of 0 and 1, with the proviso that not both of e and f are 0,
- $R_1$ and $R_2$ are either hydrogen or form an alkyl($C_1$–$C_4$) benzene ring or an alkoxy($C_1$–$C_4$) benzene ring together with $C_1$ and $C_2$, wherein $C_2$ is the para position,
- $R_3$ and $R_4$ are either hydrogen or form an alkyl($C_1$–$C_4$) benzene ring or an alkoxy($C_1$–$C_4$) benzene ring together with $C_3$ and $C_4$, wherein $C_3$ is the para position,
- $R_5$ and $R_6$ are either hydrogen or form a benzene ring or a naphtalene ring together with $C_5$ and $C_6$,
- $R_7$ and $R_8$ are either hydrogen or form an alkyl($C_1$–$C_4$) benzene ring or an alkoxy($C_1$–$C_4$) benzene ring together with $C_7$ and $C_8$, wherein $C_8$ is the para position,
- $R_9$ and $R_{10}$ are either hydrogen or form an alkyl($C_1$–$C_4$) benzene ring or an alkoxy($C_1$–$C_4$) benzene ring together with $C_9$ and $C_{10}$, wherein $C_9$ is the para position,
- X is a luminophoric moiety in ortho, para or meta position with respect to the nitrogen and m is selected from the group consisting of 0, 1 and 2.

The triaza-cryptands of the above general Formula I are novel. These novel luminophore-ionophores have been found to be very useful for determining alkali ions and to be particularly useful for determining potassium ions.

DETAILED DESCRIPTION OF THE INVENTION

Figure 1:
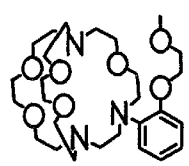
FIG. 1 depicts examples of ionophores (triaza-cryptands) in accordance with the invention.
Figure 1:
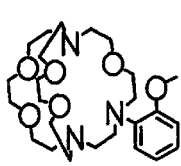
Figure 1:
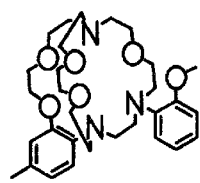
Figure 1:
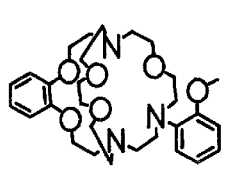
Figure 1:
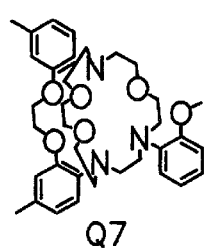
Figure 1:
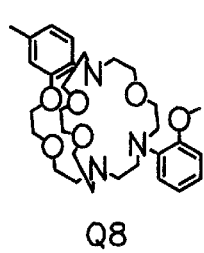
Figure 1:
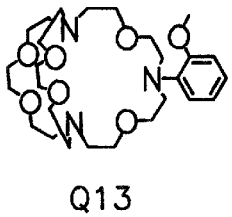
Figure 1:
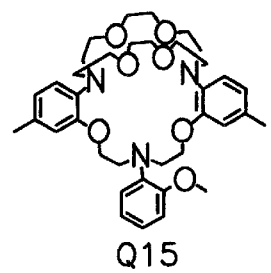
Figure 1:
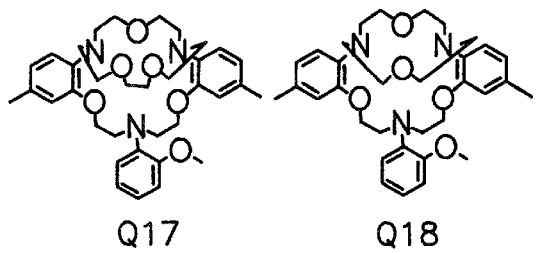
Figure 1:
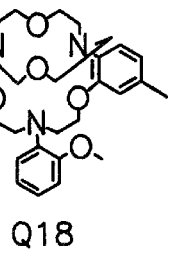
Figure 1:
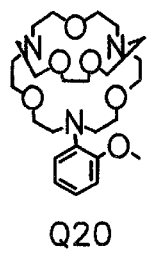
Figure 1:
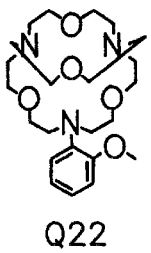
Figure 1:
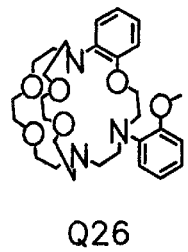
Figure 1:
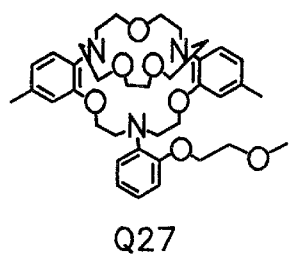
Figure 1:
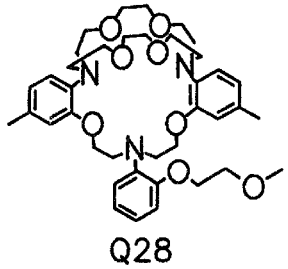
Figure 1:
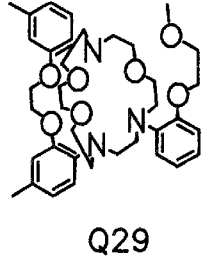
Figure 1:
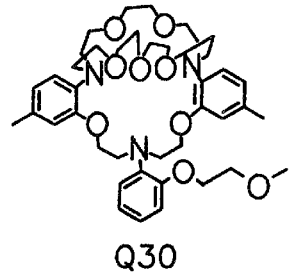

Suitable luminophoric moieties X would encompass all those moieties by which, in combination with the ionophoric moiety, a PET effect can be achieved. A great number of luminophoric moieties are known from the literature, which, in combination with the ionophore, give a PET effect or, in principle, are suitable for that purpose. By coupling these known moieties to the benzene ring of the general Formula I, new compounds are obtained, which may be examined by one skilled in the art in order to find out whether a PET effect can be obtained. Coupling may be in a position ortho to the (non-bridging) nitrogen, in its two meta positions and in the para position. The para position is the preferred position.

Those skilled in the art will be aware that in order for a PET effect to materialize it is essential, in particular, that the electron donor (the non-bridging nitrogen) of the ionophoric moiety is electronically decoupled from the electronic system of the luminophoric moiety. As is well known in the art, such electronic decoupling of the ionophoric and luminophoric moieties may be achieved in that the two moieties present are separated either by a spacer group, i.e., the $(CH_2)_m$ chain with m>0 or—if m=0—by a virtual spacer (e.g. by pivoting the plane of the luminophoric moiety to the plane of the benzene ring). Hence, the function of the spacer is to oppose conjugation of the electron system of the ionophoric moiety with the electron system of the luminophoric moiety.

Electronic decoupling can be recognized f.i. from the fact that the binding of an ion does not cause any significant change in respect of the wavelengths of the absorption and emission spectra.

The luminophoric moiety X in general Formula I preferably is an aminonaphthalimide group having the general Formula II

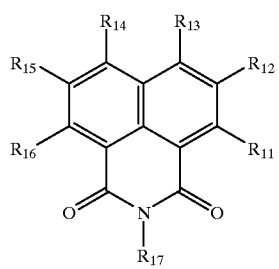

(II)

wherein at least one of $R_{11}$, $R_{12}$, $R_{13}$, $R_{14}$, $R_{15}$ and $R_{16}$ is an —NH—group through which X is bound to the group —$(CH_2)_m$— and the remaining groups and $R_{17}$ independently are selected from the group consisting of hydrogen, a lipophilic group, a hydrophilic group and a reactive group for coupling to a polymer, or is a xanthenone group having the general formula III

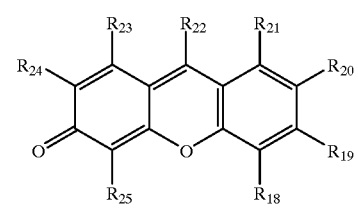

(III)

wherein m=0 and at least one of $R_{18}$, $R_{19}$, $R_{20}$, $R_{21}$, $R_{22}$, $R_{23}$, $R_{24}$, and $R_{25}$ represents a chemical bond through which X is bound directly to the ionophoric moiety and the remaining groups are each selected from the group consisting of —OH, —$OR_{26}$, wherein $R_{26}$ is a hydrophilic or a lipophilic group, —O—$R_{27}$—G, wherein $R_{27}$ is a hydrophilic or a lipophilic group and G is a reactive group for coupling to a polymer, and —$(CH_2)_n$—COOH, wherein n is a number between 0 and 17, or is a compound having the general Formula IV

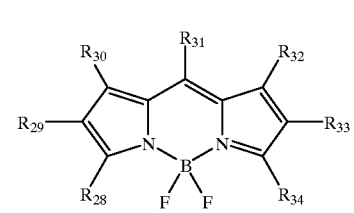

(IV)

wherein at least one of $R_{28}$, $R_{29}$, $R_{30}$, $R_{31}$, $R_{32}$, $R_{33}$ und $R_{34}$ represents a chemical bond through which X is bound to the group —$(CH_2)_m$— and the remaining groups independently are selected from the group consisting of hydrogen, a lipophilic group, a hydrophilic group and a reactive group for coupling to a polymer or a biomolecule, or $R_{29}$ forms an aromatic ring system together with $R_{30}$ and $R_{33}$ forms an aromatic ring system together with $R_{34}$.

It is preferred that in the general Formula II $R_{13}$ or $R_{14}$ are the group —NH— through which the luminophoric moiety is bound to the group —$(CH_2)_m$— of the above-mentioned general Formula I.

It is further preferred that in the general Formula III $R_{22}$ is a chemical bond through which the luminophoric moiety is bound directly (m=0) to the ionophoric moiety of the above-mentioned general Formula I.

It is preferred that in the general Formula IV $R_{31}$ is a chemical bond through which the luminophoric moiety is bound to the ionophoric moiety of the above-mentioned general Formula I. Preferably, in the general Formula IV $R_{30}$ and $R_{32}$ are independently hydrogen or methyl.

It is further preferred that in the general Formula IV the groups $R_{28}$ and $R_{34}$ represent a lipophilic group, in particular, a tert. butyl each.

The following substitution patterns are particularly preferred for the compound having the general Formula IV:

Pattern 1:
  $R_{31}$: ionophoric moiety;
  $R_{28}$, $R_{34}$: lipophilic group, preferably t-butyl;
  $R_{30}$, $R_{32}$: independently —$CH_3$ or H;
  $R_{29}$ or $R_{33}$: acid group, preferably propionic acid group for immobilization;

Pattern 2:
  $R_{31}$: ionophoric moiety;

R$_{28}$, R$_{34}$: lipophilic group, preferably t-butyl;

R$_{30}$: independently —CH$_3$ or H;

R$_{32}$: acid group, preferably propionic acid group for immobilization;

Pattern 3:

R$_{31}$: ionophoric moiety;

R$_{28}$: lipophilic group, preferably t-butyl;

R$_{30}$, R$_{34}$, R$_{32}$: independently —CH$_3$ or H;

R$_{33}$: acid group, preferably propionic acid group for immobilization.

Suitable lipophilic groups are f.i. substituted and unsubstituted alkyl groups and alkoxy groups having up to 20 C atoms.

Suitable hydrophilic groups are f.i. alkyl groups having 1–17 C atoms and carrying at least one hydroxyl group and/or functional groups which at the pH of the measuring solution are present in a dissociated condition, such as f.i. carboxylic acids, sulfonic acids and phosphoric acids.

Reactive groups for coupling to aminofunctionalized polymers, f.i. aminocellulose and arninofinctional polyacrylamides, are known f.i. from U.S. Pat. No. 4,774, 339, Table 4.

These above-mentioned luminophoric moieties, which are preferably utilized, may be excited using light of wavelengths >400 nm.

Preferably, the luminophoric moiety X in general Formula I is a luminescent metal ligand complex. Luminescent long-lifetime transition metal ligand complexes with α-diimine ligands selected from the group of 2,2'bipyridine, 1,10-phenanthroline and 4,7-diphenyl-1,20-phenanthroline, which ligands contain, for instance, a central atom of the group consisting of ruthenium(II), osmium(II), iridium(III) and rhodium(III) are particularly suitable.

Figure 2:
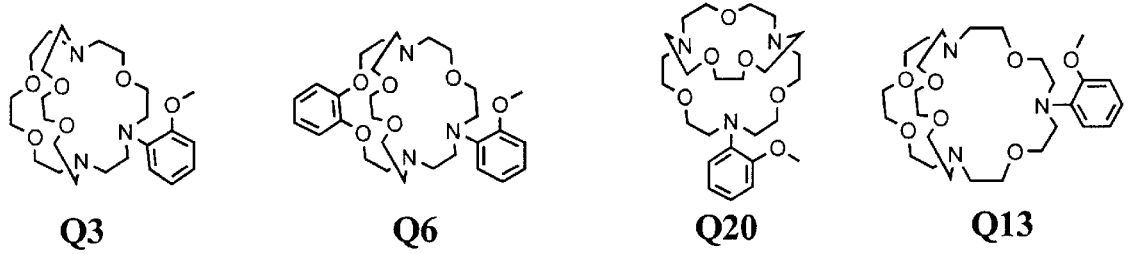
FIG. 2 depicts ionophores in accordance with the invention grouped according to all aliphatic, aliphatic/aromatic and all aromatic bridging nitrogens, respectively.
Figure 2:
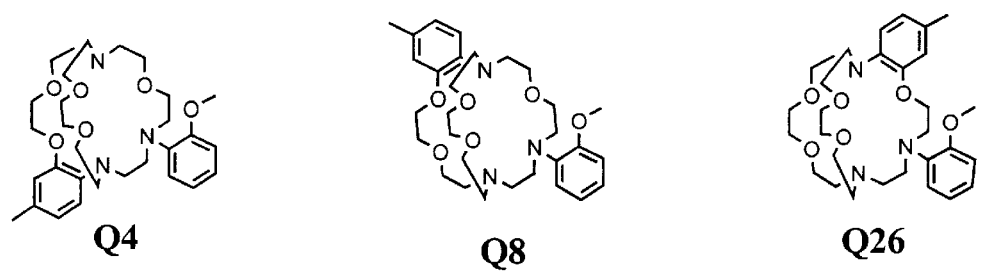
Figure 2:
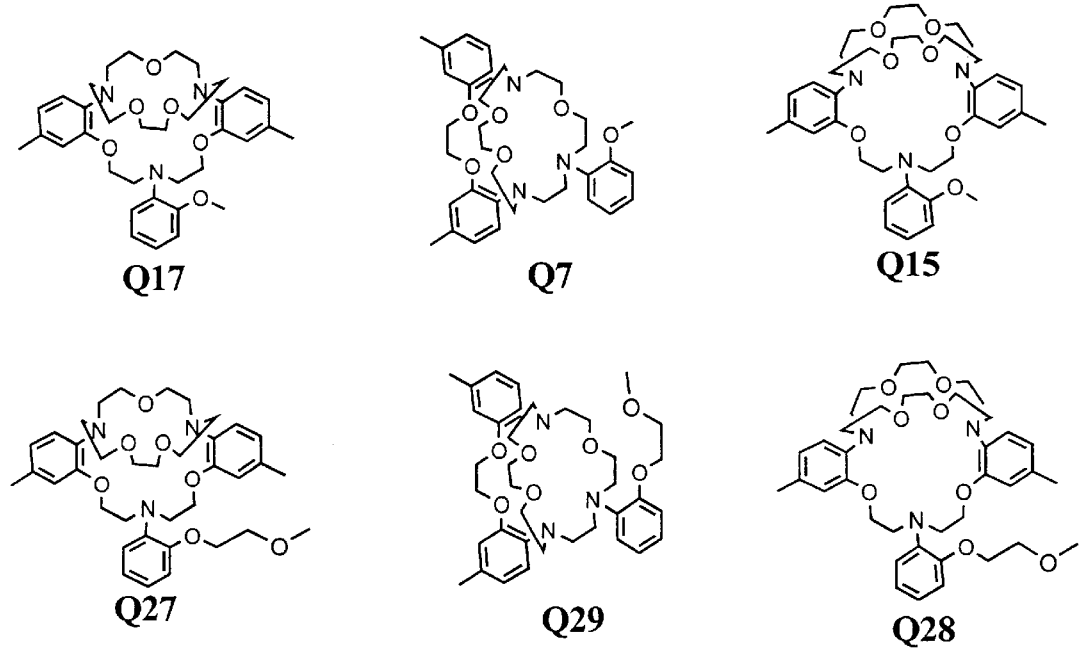
Figure 3:
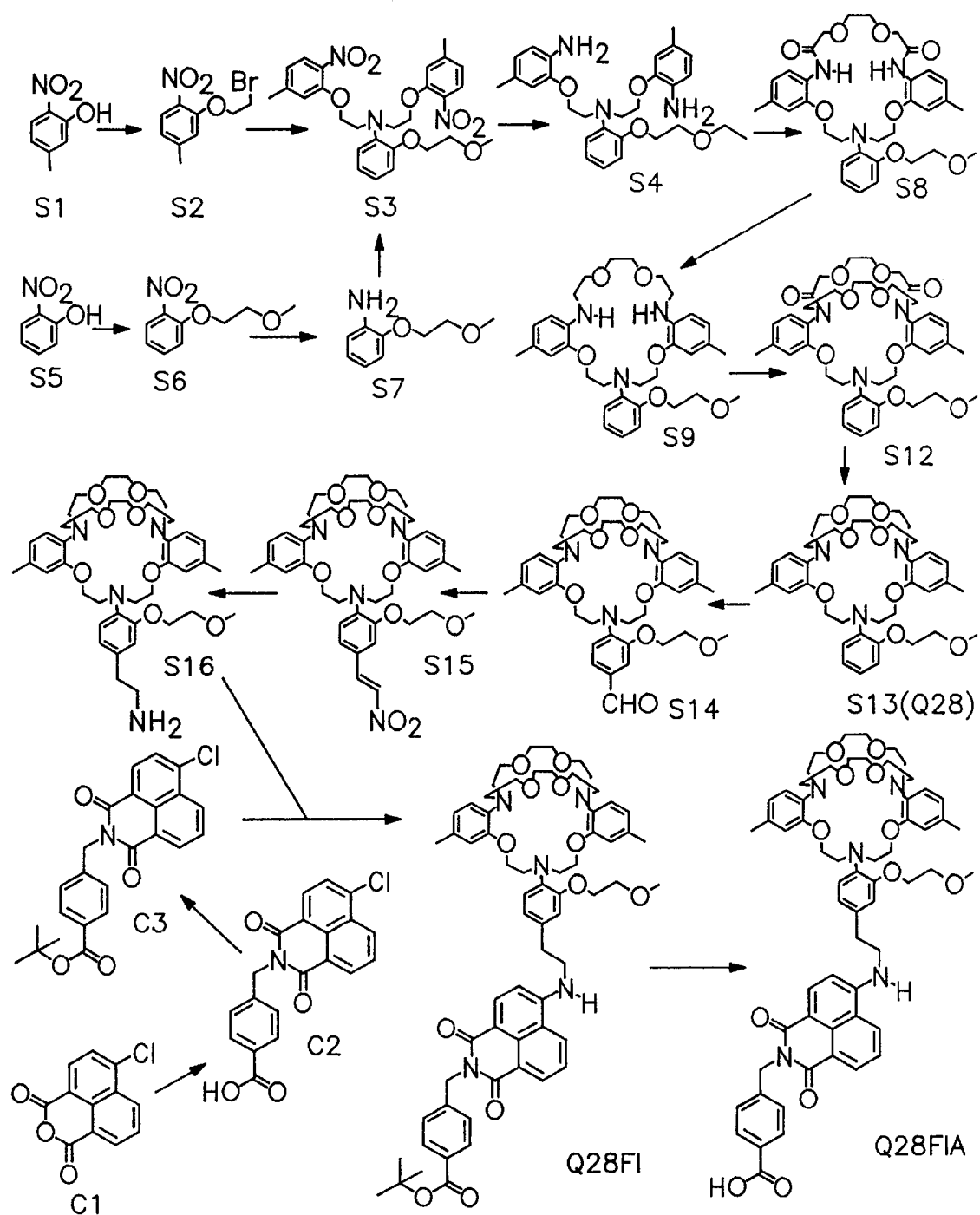
FIG. 3 is an illustration of a synthetic pathway for a triaza-cryptand (Q28) and a luminophore-ionophore (Q28FI and Q28FIA) in accordance with the invention.
Figure 4:
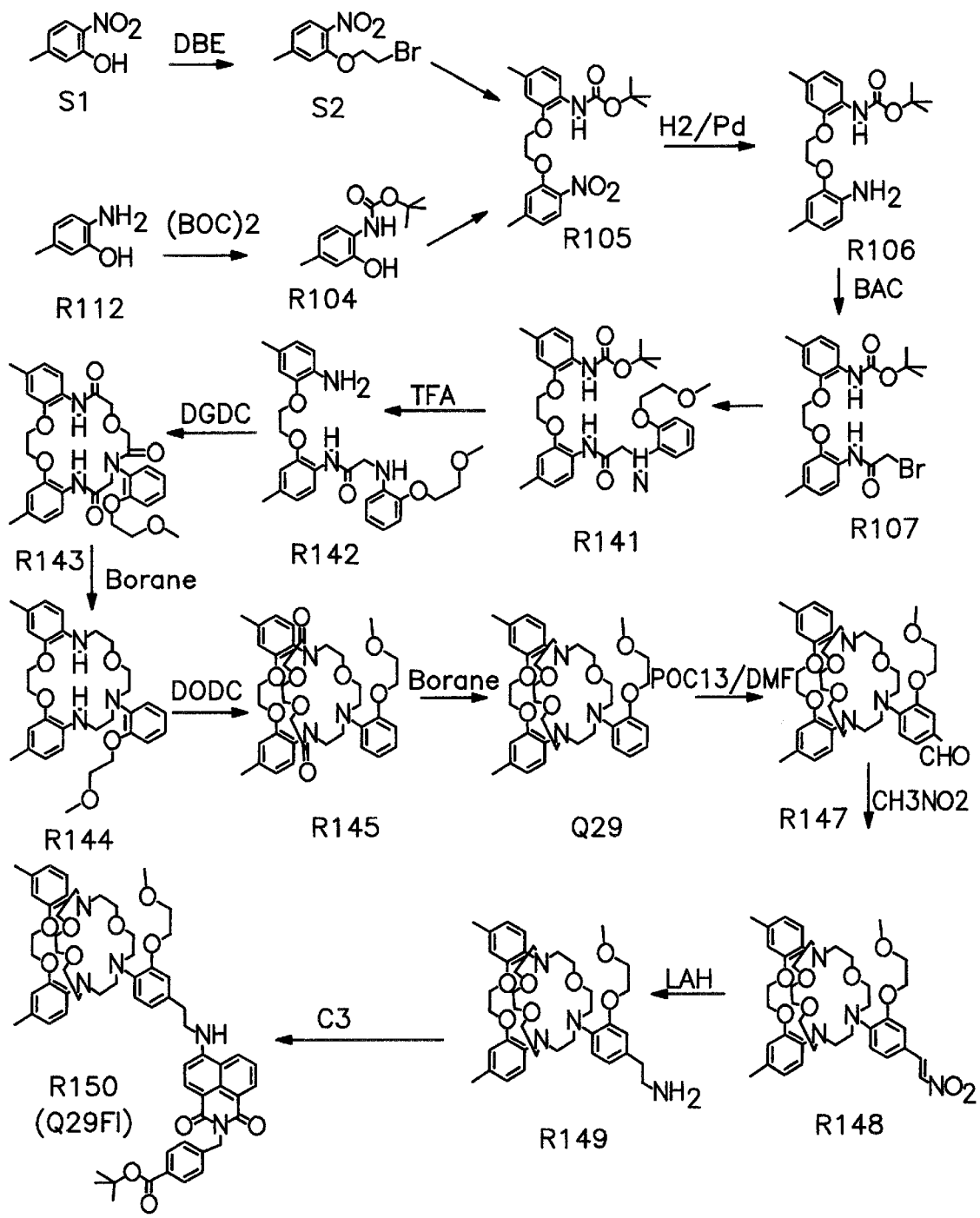
FIG. 4 is an illustration of a synthetic pathway for a triaza-cryptand (Q29) and a luminophore-ionophore (Q29FI) in accordance with the invention.

Examples of ionophores (triaza-cryptands) in accordance with the invention are shown in FIGS. 1 and 2. In FIG. 2 the ionophores are grouped according to all aliphatic, aliphatic/aromatic and all aromatic bridging nitrogens, respectively. It should be noted that in the chemical structures depicted in FIGS. 1, 2, 3 and 4 any single bond with a free end represents a —CH$_3$ group. For example, the structure of Q28 depicted in FIGS. 1, 2 and 3 as

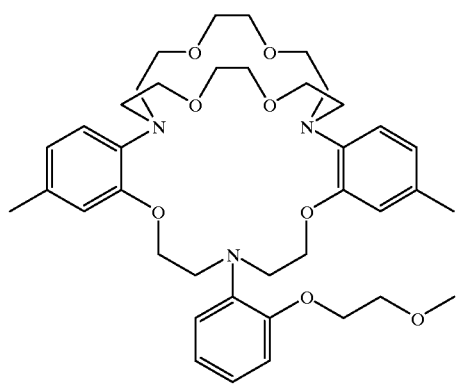

Q28 should read

-continued

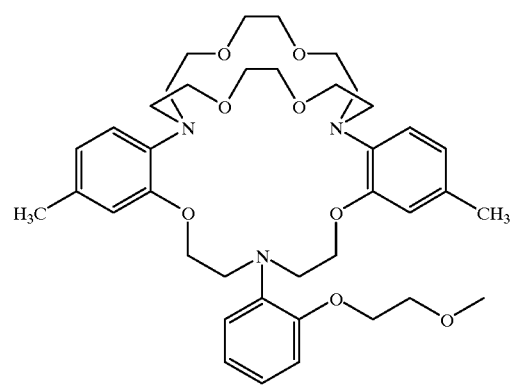

Q28

It is preferred that in the triaza-cryptands according to the invention each of the three nitrogens of the cryptand is bound to at least one aryl group. Such luminophore-ionophores are particularly useful for determining alkali ions at pH values above 6.5.

For determining potassium ions, a triaza-cryptand with three aryl nitrogens of the general Formula I is preferably used, in which a=1, b=1, c=1, d=2, e=1, f=1, R$_3$, R$_4$, R$_5$, R$_6$, R$_7$ and R$_8$ are hydrogen, R$_1$ and R$_2$ form a toluene ring together with C$_1$ and C$_2$, wherein C$_2$ is the para position, and R$_9$ and R$_{10}$ form a toluene ring together with C$_9$ and C$_{10}$, wherein C$_9$ is the para position.

For determining sodium ions, a triaza-cryptand with three aryl nitrogens of the general Formula I is preferably used, in which a=0, b=1, c=1, d=1, e=0, f=1, R$_3$, R$_4$, R$_5$ and R$_6$ are hydrogen, R$_1$ and R$_2$ form a toluene ring together with C$_1$ and C$_2$, wherein C$_2$ is the para position, and R$_9$ and R$_{10}$ form a toluene ring together with C$_9$ and C$_{10}$, wherein C$_9$ is the para position.

The triaza-cryptands of the invention for determining alkali ions may be added to the sample solution in the dissolved state. However, they may also be components of a sensor, where they may be embedded in a layer formed f.i. from a hydrogel, as will be described below with reference to FIG. 5.

The present invention also provides a method of determining an alkali ion in a sample, comprising the steps of:

providing a compound having a luminophoric moiety and an ionophoric moiety, reacting the ionophoric moiety with the alkali ion present in the sample, wherein the luminophoric moiety changes its luminescence properties, measuring the luminescence, and determining the presence of the alkali ion in the sample utilizing the measured luminescence, wherein the compound is a triaza-cryptand according to the invention.

In the context of the present invention the expression "measuring the luminescence" refers to the measurement of any luminescence property, including the measurement of luminescence intensity, time-resolved measurements of decaying luminescence intensity and phase modulation measurements.

The determination of the alkali ion (analyte ion) in the sample utilizing the measured luminescence can be based on luminescence intensity or on luminescence decay time.

1. Intensity based determination of the concentration of the analyte ion with a luminophore-ionophore according to the invention:

The reversible binding of the cation (M) to be determined and the reversible binding of interfering cations ($N_i$) to the ionophore (I) proceeds according to the principle of mass action law (Equation 1):

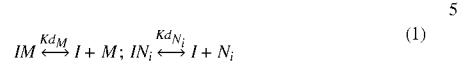

$$IM \overset{Kd_M}{\longleftrightarrow} I + M; \quad IN_i \overset{Kd_{N_i}}{\longleftrightarrow} I + N_i \qquad (1)$$

wherein, at a given ionic strength and temperature, the dissociation constant (Kd) is given by Equation 2

$$Kd_M = \frac{cIcM}{c(IM)}; \quad Kd_N = \frac{cIcN}{c(IN)} \qquad (2)$$

wherein I denotes the ionophore, IM the ionophore-ion complex and c the concentration. In the following Kd is given in mol/l.

The binding constant K (Equation 3) is related to Kd by $$K = \frac{1}{Kd} \qquad (3)$$

and is given in 1/mol.

Preferred ionophores for determining the cation M have Kd values differing by less than factor 0.1–10 from the expected target concentrations of M.

In case the ionophore is cross-sensitive to other cations $N_i$ (interfering cations), competitive binding will occur between the analyte M and the interfering cations $N_i$. Index i denotes the ith interfering cation. For no significant cross sensitivity to be present from an interfering cation $N_i$ present in the sample, it is required that $Kd_{Ni}$ is higher at least by a factor 10–100 as compared to the concentration of $N_i$ in the sample. In case $Kd_{Ni}$ differs from $cN_i$ by a factor 0.1–10, correction is required and the method is applicable to samples where $cN_i$ is known. In cases $Kd_{Ni}$ is lower than $cN_i$ by a factor 0.1, a saturation of the ionophore with the interfering cations $N_i$ will occur and the ionophore is not suitable for determination of the analyte ion M with the given type of sample.

At given excitation and emission wavelengths, the relative luminescence intensity is the superposition of the relative luminescence intensities of all luminophore-ionophore species:

$$S = S_L + S_{LM} + \sum_i S_{LNi} \qquad (4)$$

where S denotes the relative luminescence intensity, L denotes the free luminophore-ionophore, LM denotes the luminophore-ionophore with a bound analyte ion M, and LNi denotes the luminophore-ionophore with a bound interfering ion $N_i$.

Binding of an ion to the ionophoric moiety of L partially or completely inhibits the PET effect and the overall luminescence intensity is given by Equation 5

$$S = k_o cL + k_m c(LM) + \sum_i^{i=1,n} k_i c(LN_i) \qquad (5)$$

where c denotes concentration, $k_o$, $k_m$ and $k_i$ are factors relating the concentrations of L, LM and $LN_i$, respectively, to the concentration of the individual luminophore-ionophore species.

The relative luminescence intensity S of the luminophore-ionophore is obtained as a function of cM and $cN_i$ according to Equation 6:

$$S = Sm_M \left( 1 + \frac{qo - 1 + \sum_{i=1}^{n}((q_i - 1)K_{N_i}cN_i)}{1 + \sum_{i=1}^{n}(K_{N_i}cN_i) + K_M cM} \right) \qquad (6)$$

$Sm_M$ is the relative luminescence intensity of the luminophore-ionophore fully saturated with the analyte ion M. qo=ko/km is a factor indicating the luminescence intensity of L relative to the luminescence intensity of LM, and $q_i$=ki/km is a factor indicating the luminescence intensity of $LN_i$ relative to the luminescence intensity of LM. $K_M$ and $K_{Ni}$ are the formation constants of the ionophore-ion complexes.

Solving Equation 6 for cM yields an equation for determining the concentration of the analyte ion M in a sample:

$$cM = \frac{1}{K_M} \left( \frac{qo - 1 + \sum_{i=1}^{n}((q_i - 1)K_{N_i}cN_i)}{\frac{S}{SmM} - 1} - 1 - \sum_{i=1}^{n}(K_{N_i}cN_i) \right) \qquad (7)$$

S is the relative luminescence intensity of the luminophore-ionophore in (binding) equilibrium with the ions of the sample. Qo, $q_i$, $K_{Ni}$ and $K_M$ are parameters specific for a luminophore-ionophore according to the invention, dissolved in the sample or present in a hydrophilic matrix. These parameters are temperature dependent and can be determined as shown in the Examples. $cN_i$ is the concentration of the ith interfering ion in the sample. In case there is no interfering ion or the product $K_{Ni} cN_i$ becomes small due to low values of $K_{Ni}$ and/or $cN_i$, the "SUM" expressions are insignificant and can be omitted.

For a given measuring situation or a given sensor, $Sm_M$ can be determined via a 1 point calibration from Equation 8:

$$Sm_M = \frac{S_{cal}}{\left( 1 + \frac{qo - 1 + \sum_{i=1}^{n}(q_i - 1)K_{N_i}cN_{i,cal}}{1 + \sum_{i=1}^{n}(K_{N_i} + cN_{i,cal}) + K_{M+}cM_{cal}} \right)} \qquad (8)$$

Qo, $q_i$, $K_{Ni}$ and $K_M$ have the same meaning as in Equation 7. $cM_{cal}$ and $cN_{i,cal}$ are the concentrations of the analyte ion and the interfering ion(s) in the calibration liquid. The calibration liquid may or may not contain interfering ions.

Substitution of $Sm_M$ in Equation 6 with Equation 8 yields an equation for determining the concentration of the analyte ion M of the sample based on the known parameters of the sensor (Qo, $q_i$, $K_{Ni}$ and $K_M$), the known concentrations of $M_{cal}$ and $N_{i,cal}$ of analyte and interfering ions, respectively, in the calibration medium, the relative luminescence intensity $S_{cal}$ of the sensor in the presence of the calibration medium, the relative luminescence intensity S of the sensor in the presence of the sample to be determined, and, if present, the known (measured) concentrations of interfering ions $N_i$.

Thus, there is also provided a method of determining an alkali ion in the sample, wherein the relative luminescence intensity of a luminophore-ionophore according to the invention in contact with the ions of the sample is measured and the concentration of the alkali ion is determined utilizing the measured luminescence by a method comprising the steps of calibrating the luminophore-ionophore in a calibration medium, wherein the relative luminescence intensity $Sm_M$ of the luminophore-ionophore fully saturated with the analyte alkali ion M is determined according to Equation 8 as cited above and determining the concentration cM of the analyte alkali ion M in the sample according to Equation 7 as cited above.

2. Decay time based determination of the concentration of an analyte ion with a luminophore-ionophore according to the invention:

(Reference: S. Draxler, M-E. Lippitsch, Sensors and Actuators B 29 (1995) 199–203).

When the luminophoric part of the luminophore-ionophore is excited, there exists a certain probability of an electron transfer (PET) from the ionophore part to the luminophore part. This process competes with the luminescence emission and hence influences the luminescence decay time. For the free indicator species L, the PET rate is a maximum and the luminescence decay time is a minimum. For the indicator species LM, the PET rate decreases and the luminescence decay time is higher as compared to the luminescence decay time of the free indicator. The PET rate (and hence the luminescence decay time) depends on the type of the ion bound. Since bound and unbound indicator molecules (L, LM, $LN_i$) with individual luminescence decay times are present, to an extent depending on the Kd values and the concentration of ions in the surrounding medium, the overall decay S(t) is the superposition of the decays of the individual species. Accordingly, the time-dependent luminescence intensity is obtained from Equation 9:

$$S(t) = A_L e^{\left(-\frac{t}{\tau_L}\right)} + A_{LM} e^{\left(-\frac{t}{\tau_{LM}}\right)} + \sum_i A_{LN_i} e^{\left(-\frac{t}{\tau_{LN_i}}\right)} \qquad (9)$$

where S(t) is the time-dependent luminescence intensity after switching off the excitation light, the subscripts L, LM and $LN_i$ refer to the bound and unbound forms of the indicator, $\tau_L, \tau_{LM}$ and $\tau_{LNi}$ are the respective decay times for the bound and unbound forms and $A_L$, $A_{LM}$ and $A_{Ni}$ are pre-exponential factors of the respective species.

$A_L, A_{LM}$ are related to the concentration of the analyte ion by Equation 10:

$$cM = Kd_M q_o \frac{A_{LM}}{A_L} \qquad (10)$$

where qo has the same meaning as in Equation 6, $Kd_M$ is the dissociation constant of the indicator-ion complex and cM is the concentration of the analyte ion. $\tau_L, \tau_{LM}$, qo and $Kd_M$ are parameters specific for a given luminophore-ionophore according to the invention, dissolved in a sample or present in a hydrophilic ion-permeable material (sensor) in contact with the sample.

Known methods for decay-time based measurements include time-resolved and phase-modulation techniques. Both phase-modulation and time-resolved methods are well known in the art (cf. Lakowicz, Principles of Fluorescence Spectroscopy, Plenum Press, 1993, Chapter 3).

In time-resolved measurements the decaying luminescence intensity S(t) after irradiation is detected. From Equation 9, the ratio $A_{LM}/A_L$ can be processed based on the known parameters $\tau_L, \tau_{LM}$ and $\tau_{LNi}$. Finally, the concentration of the analyte ion is calculated from the ratio $A_{LM}/A_L$ and the known parameters qo and $Kd_M$ (Equation 10).

Thus, there is provided a further method of determining an alkali ion in the sample wherein the time-dependent luminescence intensity of the luminophore-ionophore in contact with the ions of the sample is measured after switching off the excitation light and the concentration of the alkali ion is determined utilizing the measured time-dependent luminescence by determining the concentration cM of the analyte alkali ion M in the sample according to Equations 9 and 10 as cited above.

In phase-modulation techniques the indicator is irradiated, preferably in a sinusoidal manner. The time lag between excitation and luminescence causes the luminescence to be shifted in phase and demodulated relative to the amplitudes of the excitation radiation. The phase shift depends on the known Kd values, the decay times and the amplitudes of the bound and unbound indicator species. The phase shift can be determined and used to calculate the concentration of the analyte ion.

Most of the luminophoric moieties known so far display decay times below 100 ns, which requires relatively fast and expensive electronics for time-domain decay-time measurements or modulation frequencies >10 MHz for frequency-domain measurements. For decay-time based measurements, it is, therefore, desirable to select luminophoric moieties with long decay times (i.e., >100 ns) such as transition metal ligand complexes or certain lanthanides requiring slower electronics and modulation frequencies.

In contrast to intensity-based measurements, decay-time based measurements are within certain limits mostly independent of the indicator concentration, the intensity of the light source, the sensitivity of the light detector and characteristics of the optical components. Decay-time based measurements may be unaffected by photo bleaching or washout of the indicator.

Therefore, luminescence decay-time based measurements offer the possibility to be performed without calibration prior to measurement and/or without frequent recalibration in monitoring applications (continuous measurements). Decay-time-based measurements are preferred in measuring situations where it is difficult to calibrate (i.e., indicator added to the sample).

From Equations 9 and 10, which specifically have been devised for PET type luminophore-ionophores, it can be seen that with certain restrictions no corrections for interfering ions present in the sample are required when determining the analyte ion based on luminescence decay time measurements. Furthermore, it can be seen from those equations that under certain provisions it is principally possible to determine several analyte ions with a single luminophore-ionophore by the luminescence decay time method.

The invention further provides an optical sensor for determining alkali ions in a sample, which sensor has a matrix comprising a compound having a luminophoric moiety and an ionophoric moiety, wherein the compound is a triaza-cryptand according to the invention.

In addition, the invention relates to the use of a triaza-cryptand according to any one of claims 1 to 5 in an optical sensor for the determination of alkali ions in a sample.

In the following, the invention will be described in more detail by way of examples, in which the synthesis and properties of some triaza-cryptands which are preferably used will be explained. Other compounds in accordance with the invention can be prepared in an analogous manner by a person skilled in the art.

General description of syntheses of triaza-cryptands in accordance with the invention The general strategy of syntheses of side-armed triaza-cryptands is to first synthesize triaza-containing intermediates, triazacrown ethers, and to then cyclize with diacid chloride using high dilution conditions. We did not succeed in preparing diacid chloride containing a tertiary nitrogen in the same molecule. This may be due to self-catalyzed decomposition by the tertiary amine. Except for Q4, Q7, Q8 and Q29, most of the cryptands may be prepared according to the following procedure. Paramethylnitrophenol (S1) is alkylated with a large excess of dibromoethane to give bromoethoxynitrophenylether, which is used to dialkylate the trigger aniline with different side-arm (S7) in order to obtain dinitrophenoxyalkyl-aniline (S3). The dinitro compound is hydrogenated to afford diamine (S4), which is acylated with diacid chloride using high dilution conditions in order to obtain the cyclic diamide (S8). The diamide can be reduced to triazacrown ether (S9) with borane or LAH in THF. It is recommended to use borane in order to reduce the aromatic diamide, because we did not get a decent yield of reduction with LAH for reasons unknown. The diamine is again reacted with diacid chloride to give the tertiary amide (S12). The amide can be reduced with borane in THF to afford the ionophore (Q28). This ionophore can be formylated (S14), converted into nitrostyrene (S15) and then reduced to the primary amine (S16). This amine is then coupled with chloronaphthalimide to get the luminophore-ionophore (Q28FI).

For Q4, Q7, Q8 and Q29, the triazacrown has to be prepared by a different route due to their asymmetries. The whole route can be illustrated by the preparation of Q29 as follows:

Aminomethylphenol(R112) is selectively protected with t-BOC, and reacted with S2, hydrogenated to obtain the monoprotected diamine (R106). This diamine is acylated with bromoacetyl chloride and alkylated with side-armed aniline (S7) to give protected linear triaza compound (R141). After de-protection with TFA, the amine (R142) is acylated with diacid chloride to obtain cyclic triamide (R143), which is reduced with borane in THF to afford triazacrown ether (R144). After high dilution acylation and borane reduction, the final ionophore can be obtained at quite a good yield ranging from 50 to 80%. Similar methods can be used to obtain luminophore-ionophores.

EXAMPLE 1

2-Methoxyethoxynitrobenzene (S6)

140 g (1010 mmol) 2-nitrophenol, 105 g (1110 mmol) chloroethyl methyl ether, 84.2 g (507 mmol) KI and 153 g (1110 mmol) $K_2CO_3$, were suspended in 500 ml DMF, in a 2 l Erlenmeyer flask heated at 110±5° C. for 6 h. The solvent was evaporated and the residue was dissolved in 500 ml $CHCl_3$ and 500 ml water. The organic phase was washed with 2×500 ml 2.5% $Na_2CO_3$, 500 ml sat. NaCl and dried over $Na_2SO_4$. The solvent was evaporated to afford 201 g (100%) light yellow oil. $H^1NMR$ ($CDCl_3$) δ (ppm) 3.45 (s,3H), 3.78(t,2H), 4.25(t,2H), 7.02(dd,1H), 7.10(dd,1H), 7.50(dd,1H), 7.82(dd,1H).

EXAMPLE 2

2-Methoxyethoxy aniline (S7)

3.05 g (12.0 mmol) 2-methoxyethoxy anisidine (MEA) was dissolved in 200 ml methanol, 1.5 g 10% palladium on carbon black was added. This suspension was hydrogenated at 2.2 atm. for 18 h till no more hydrogen uptake was observed. The catalyst was filtered off and the solvent was evaporated to afford 48.7 g (102%) light yellow oil. $H^1NMR$ ($CDCl_3$) δ (ppm) 3.45 (s,3H), 3.65(br.s,2H), 3.78(t,2H), 4.25(t,2H), 6.74(m,2H), 6.82(m,2H).

EXAMPLE 3

2-(Bromoethoxy)-4-methylnitrobenzene (S2)

122.5 g (800 mmol) 5-methyl-2-nitrophenol, 751.0 g (4000 mmol) 1,2-dibromoethane, 110.7 g (800 mmol) $K_2CO_3$ were suspended in 400 ml anhydrous DMF. The suspension was heated at 120° C. for 1 hour, then cooled and most of the liquid was evaporated. The residue was dissolved in 1 l $CHCl_3$ and 1 l water. The organic layer was washed with 2×1 l of 1.8% NaOH till the aqueous layer became pale yellow. The organic layer was dried over $Na_2SO_4$ for 18 h, filtered and the solvent was evaporated to give ~240 g oil. The oil was triturated with 240 ml boiling methanol and allowed to settle for 2 h. The resultant precipitate was filtered, washed with 2×100 ml cold methanol and dried at RT for 18 h to afford 89.4 g (43%) off-white crystal. $H^1NMR$ ($CDCl_3$) δ (ppm): 2.40(s, 3H), 3.65(t,2H), 4.30(t,2H), 6.85(d,2H), 7.75(d,1H).

EXAMPLE 4

N,N-Bis[(2'-nitro-5'-methylphenoxy)ethoxy]-2-methoxyethoxy-aniline (S3)

16.7 g (100 mmol) 2-methoxyethoxy aniline (MEA), 78.0 g (300 mmol) 2-(bromoethoxy)-4-methylnitrobenzene (BMNB), 41.4 g (300 mmol) $K_2CO_3$ and 24.9 g (150 mmol) KI were suspended in 200 ml acetonitrile. The suspension was heated under reflux for 20 h. Then 26 g 2-(bromoethoxy)-4-methylnitrobenzene (BMNB) and 13.8 g (300 mmol) $K_2CO_3$ were added and heating was continued for another 18 h. After cooling the solvent was evaporated and the residue was dissolved in 500 ml $CHCl_3$ and 500 ml saturated NaCl and dried over $Na_2SO_4$. The solvent was evaporated to give 120 g oil. This oil was triturated with 120 ml boiling methanol and hot filtered. Drying at RT for 18 h afforded 30.4 g bright yellow crystal. This crystal was recrystalized from about 2 l ethanol to afford 29 g (58%) bright yellow crystal. $H^1NMR$ ($CDCl_3$) δ (ppm) 2.35(s, 6H), 3.35(s,3H), 3.70(t,2H), 3.75(t,4H), 4.10(t,2H), 4.20(t,4H), 6.85(m,8H), 7.75(d,2H).

EXAMPLE 5

N,N-Bis[(2'-Amino-5'-methylphenoxy)ethoxy]-2-methoxyethoxy-aniline (S4)

54.0 g (100 mmol) N,N-Bis[(2'-nitro-5'-methylphenoxy)ethoxy]-2-methoxy ethoxy-aniline (BEMA) was dissolved in 500 ml DMF, 17.5 g 10% palladium on carbon black was added. This suspension was hydrogenated at 2.2 psi. for 18 h till no more hydrogen uptake was observed. The catalyst was filtered off and the solvent was evaporated to afford 46.8 g (97%) light yellow oil. $H^1NMR$ ($CDCl_3$) δ (ppm) 2.20(s, 6H), 3.35(s,3H), 3.45(br.s,4H), 3.70(m,6H), 4.10(m,6H), 6.60–7.10 (m,10H).

EXAMPLE 6

3,6-Dioxa-1,8-octanedioic acid dichloride (DODC)

31.3 g (175 mmol) 3,6-dioxa-1,8-octanedioic acid was suspended in 200 ml anhydrous benzene. 62.5 g (492 mmol)

oxalyl chloride and 6 drops of pyridine were added. The mixture was stirred at RT for 20 h and most of the solvent was evaporated. The residue was re-dissolved in 200 ml benzene and the solvent was evaporated. The last step was repeated for one more time. Reduced pressure down to ~5 mmHg was applied to the oil in order to remove oxalyl chloride completely. 36.5 g (95%) product were obtained. The product was kept in a freezer for the next reaction step.

EXAMPLE 7

Bis(4-methylbenzo[5,6,17,18](O,N,N',O')-N''-(2-methoxyethoxy-phenyl)-1,7,16-triaza-21-crown-7-[8,15]di-one (S8)

46.8 g (100.6 mmol) N,N-bis[(2'-amino-5'-methylphenoxy)ethoxy]-2-methoxy-ethoxy-aniline (AEMA) and 22.4 g (221.3 mmol) triethylamine were dissolved in 500 ml anhydrous THF in a 500 ml addition funnel, while 23.8 g (110.6 mmol) 3,6-dioxa-1,8-octanedioic acid chloride were dissolved in 500 ml THF in another 500 ml addition funnel. The solutions in the two addition funnels were added slowly during 8 h into a 5 l flask containing 2.5 l anhydrous THF. The mixture was stirred at RT for 20 h. The precipitate was filtered off and the filtrate was evaporated to give 60 g white solid. The solid was triturated with 200 ml hot methanol, filtered, washed with 2×100 ml methanol and dried at RT for 18 h to give 55 g crude product. This crude product was purified with 240 g silica gel 60 using $CHCl_3$ and $CHCl_3$/MeOH (97/3, v/v) as the eluent to afford 34.1 g (55%) white powder. $H^1NMR$ ($CDCl_3$) δ (ppm) 2.25(s,6H), 3.45(s,3H), 3.75(m,2H), 3.85 (t,4H), 3.90(s,4H), 4.10(m,6H), 4.15(s,4H), 6.50–7.00(m, 6H), 8.20(d.2H), 9.10(s.2H).

EXAMPLE 8

Bis(4-methylbenzo[5,6,17,18](O,N,N',O')-N''-(2-methoxyethoxy-phenyl)-1,7,16-triaza-21-crown-7 (S9)

35.0 g (57.6 mmol) S8 was dissolved in 800 ml anhydrous THF and cooled to −5 to 0° C. with an ice-salts bath. 800 ml borane/THF complex was added during 1.5 h using a stainless steel cannula. The cooling bath was removed when the addition was complete. The mixture was allowed to warm up to RT during 2 h. The mixture was heated under reflux for 2 h and cooled to 15° C. 50 ml water was added very slowly to quench the excess of borane, till no hydrogen gas evolved. The solvent was evaporated and the residue was dissolved in 1 l of 6N HCl, heated under reflux for 3 h and stirred at RT for 18 h. The acidic solution was basified with solid NaOH to neutral pH, extracted with 2×500 ml $CHCl_3$ and dried over $Na_2SO_4$. The solvent was evaporated and the residue was purified with 120 g silica gel 60 with $CHCl_3$ as the eluent to afford 31.4 g (94%) oil, crystallized after settling at RT for 18 h. $H^1NMR$ ($CDCl_3$) δ (ppm) 2.20(s,6H), 3.30(t,4H), 3.45(s,3H), 3.70(s,4H), 3.75(m,6H), 3.85(t,4H), 4.05(t,4H), 4.15(t,2H), 6.50–7.10(m,10H).

EXAMPLE 9

Bis(4-methylbenzo[5,6,17,18](O,N,N',O')-]-N''-(2-methoxyethoxy-phenyl)-1,7,16-triaza-cryptand[3,2,2]-[8,15]di-one (S12)

11.0 g (19.1 mmol) S9 and 3.36 g (42.0 mmol) pyridine were dissolved in 100 ml anhydrous $CH_2Cl_2$ in a 125 ml addition fimnel, while 4.52 g (21.0 mmol) 3,6-dioxa-1,8-octanedioic acid chloride were dissolved in 125 ml $CH_2Cl_2$ in another 125 ml addition funnel. The solutions in the two addition funnels were slowly added during 5 h into a 1 l flask containing 400 ml anhydrous THF. The mixture was stirred at RT for 20 h. The resultant solution was washed with 2×600 ml 0.2 N HCl, 600 ml sat. NaCl and dried over $Na_2SO_4$. The solvent was evaporated and the residue was purified with 80 g silica gel 100 with $CHCl_3$ and $CHCl_3$/MeOH (97/3, v/v) to afford 10.6 g (77%) white foam. $H^1NMR$ ($CDCl_3$) δ (ppm) 2.25(d,6H), 3.45(s,3H), 3.60–4.15(m,32H), 6.50–7.00(m,10H), 7.40(br.s.2H).

EXAMPLE 10

Bis(4-methylbenzo[5,6,17,18](O,N,N',O')-]-N''-(2-methoxyethoxy- phenyl)-1,7,16-triaza-cryptand[3,2,2]. (Q28)

10.6 g (14.7 mmol) S12 was dissolved in 250 ml anhydrous THF and cooled to −5 to 0° C. with an ice-salts bath. 220 ml of 1 molar borane/THF complex were then added during 40 min using a stainless steel cannula. The cooling bath was removed when the addition was complete. The mixture was allowed to warm up to RT during 2 h. The mixture was heated under reflux for 2 h and cooled to 15° C. 10 ml water was added very slowly to quench the excess of borane, till no hydrogen gas evolved. The solvent was evaporated and the residue was dissolved in 200 ml 6N HCl, heated under reflux for 3 h and stirred at RT for 18 h. The acidic solution was basified with solid LiOH to neutral pH, extracted with 2×300 ml $CHCl_3$ and dried over $Na_2SO_4$. The solvent was evaporated and the residue was purified with 30 g silica gel 60, with $CHCl_3$ as the eluent to afford 8.4 g (83%) oil. $H^1NMR$ ($CDCl_3$) δ (ppm) 2.20(s,6H), 3.30–4.20 (m39H), 6.50–7.10(m,10H).

EXAMPLE 11

Bis(4-methylbenzo[5,6,17,18](O,N,N',O')-]-N''-(2-methoxyethoxy-4-formyl-phenyl)-1,7,16-triaza-cryptand[3,2,2](S14)

8.50 g (12.3 mmol) Q28 was dissolved in 46 ml DMF and cooled to −5 to 0° C. 18.9 g (123 mmol) $POCl_3$ was added during 1 h, while the temperature was kept below 0° C. The ice bath was removed when the addition was complete. The solution was stirred at RT for 18 h, then warmed to 70° C. for 1 h, cooled, poured into 420 ml ice water, basified with solid $Na_2CO_3$ to pH 7, extracted with 400 ml $CHCl_3$ and dried over $Na_2SO_4$. The solvent was evaporated to afford 9.08 g (102%) light yellow oil. $H^1NMR$ ($CDCl_3$) δ (ppm) 2.20(s,6H), 3.30–4.20(m39H), 6.50–7.10(m,9H), 9.75 (s.1H).

EXAMPLE 12

Bis(4-methylbenzo[5,6,17,18](O,N,N',O')-]-N''-(2-methoxyethoxy-4-nitrovinyl-phenyl)-1,7,16-triaza-cryptand[3,2,2](S15)

9.05 g (12.3 mmol) S14, 16.6 g (271 mmol) nitromethane, 9.50 g (136 mmol) $NH_4Ac$ were suspended in 40 ml acetic acid. The suspension was heated at 55 to 60° C. for 4 h, then poured into 420 ml water, extracted with 400 ml $CHCl_3$ and dried over $Na_2SO_4$. The solvent was evaporated to afford 6.40 g red oil. This oil was purified with 30 g silica gel 60, with $CHCl_3$ as the eluent to afford 5.85 g (62%) red oil. $H^1NMR$ ($CDCl_3$) δ (ppm) 2.20(s,6H), 3.30–4.20(m39H), 6.50–8.10(m,11H).

EXAMPLE 13

Bis(4-methylbenzo[5,6,17,18](O,N,N',O')-]-N"-(2-methoxyethoxy-4-aminoethyl-phenyl)-1,7,16-triaza-cryptand[3,2,2](S16)

5.85 g (7.69 mmol) S15 in 80 ml THF was added during 1 h to a boiling suspension containing 4.38 g (115 mmol) of $LiAlH_4$ in 230 ml THF. Heating was continued under reflux for 5 h. After quenching with 5 N LiOH, filtration and washing with 2×200 ml THF, the solvent was evaporated to get 5.3 g oil. This oil was purified with 16 g silica gel 100, using $CHCl_3$ and $CHCl_3$/methanol to get 2.47 g (44%) clear oil. $H^1NMR$ ($CDCl_3$) δ (ppm) 2.00(br.s,7H/H2O), 2.20(s, 6H), 2.65(t,2H), 2.95(t,2H), 3.30–4.20(m.39H), 6.50–7.10 (m,9H).

EXAMPLE 14

4-Chloro-1,8-naphthalimidylmethyl benzoic acid (C2)

46.4 g (200 mmol) 4-chloro-1,8-naphthalic anhydride and 30.2 g (200 mmol) 4-aminomethyl benzoic acid were suspended in 1 l DMF. The suspension was stirred at RT for 16 h and at 60° C. for 6 h. The mixture was poured into 3 l water and the pH was adjusted to 4 with 6N HCl. The resultant precipitate was filtered and dried at 60° C. for 18 h to afford 36 g (51%) off-white powder. $H^1NMR$ ($CDCl_3$) δ (ppm) 5.30(s,2H), 7.45(d,2H), 7.85(d,2H), 8.02(q,2H), 8.45(d,1H), 8.60(t,2H).

EXAMPLE 15 t-Butyl 4-chloro-1,8-naphthalimidylmethyl benzoate (C3)

29.2 g (80 mmol) C2 was suspended in 320 ml DMF and stirred at 40° C. for 20 min under a stream of nitrogen. 52.0 g (320 mmol) 1,1'-carbonyldiimidazole was added slowly during 20 min. The suspension turned into a clear solution and became turbid again in 15 min. Then the mixture was warmed to 70° C. and kept at this temperature for 18 h after the addition of 52 ml (1600 mmol) t-butanol and 48 ml (320 mmol) 1,8-diazabicyclo(5,4,0)undec-7-ene (DBU). The mixture was cooled and poured into 2.0 l icy 1N HCl under vigorous stirring. The resultant precipitate was filtered, washed with 2×300 ml 1N HCl and dried in a dessicator with $P_2O_5$ for 18 h to afford 28.5 g crude product. This crude product was purified with a silica gel column with $CHCl_3$/cyclohexane to give 12.0 g white powder (36%). $H^1NMR$ ($CDCl_3$) δ (ppm) 1.50 (s,9H), 5.30(s,2H), 7.45(d,2H), 7.80 (d,2H), 8.05(q,2H), 8.50(d,1H), 8.60(t,2H).

EXAMPLE 16 t-ButylN-{bis(4-methylbenzo[5,6,17,18](O,N,N', O')-]-1,7,16-triaza-cryptand[3,2,2]-2-methoxyethoxy-phenylethylamino]-1', 8',-naphthalimidylmethyl}benzoate (Q28FI)

2.40 g (3.4 mmol) S16 and 1.42 g (3.4 mmol) C3 were suspended in 7.6 ml N-methylpyrrolidinone (NMP) and heated at 85° C. for 18 h. The mixture was cooled and poured into 380 ml water. The resultant precipitate was filtered and washed with 3×20 ml water. The precipitate was dissolved in $CHCl_3$, washed with 200 ml $CHCl_3$, dried over $Na_2SO_4$ and the solvent was evaporated to get 3.9 g crude product. The crude product was purified with a silica gel column using $CHCl_3$ as the eluent to afford 1.05 g (29%) pure product. $H^1NMR$ ($CDCl_3$) δ (ppm): 1.55 (s,9H), 2.20 (s6H), 3.05(t,2H), 3.35–4.05(m,41H), 5.40(s,2H), 6.65–8.60 (aro,18H). FABMS (70eV,m-nitrobenzyl alcohol dispersion with LiI): 1123 (100%), ($M+H^+$); 951 (17%), (de-benzylated+$Li^+$); 722 (11%) (ethylcryptand+$H^+$).

Examples 11 to 16 describe the coupling of the ionophore Q28 to the t-butyl ester of a naphthalimide luminophore (C3). The coupling of the ionophores Q27, Q17, Q7 and Q3 to the naphthalimide luminophore was carried out in an analogous manner to afford the compounds Q27FI, Q17FI, Q7FI and Q3FI.

EXAMPLE 17

N-{Bis(4-methylbenzo[5,6,17,18](O,N,N',O')-]-1,7,16-triaza-cryptand-[3,2,2]-2-methoxyethoxy-phenylethylamino]-1',8',-naphthalimidylmethyl}benzoic acid (Q28FIA)

1 ml trifluoroacetic acid (TFA) was added to a solution of 0.20 g (0.18 mmol) of Q28FI in 4 ml $CH_2Cl_2$. The resultant solution was stirred at RT for about 1 h when the TLC indicated that most of Q28FI was gone. The mixture was diluted with 20 ml $CHCl_3$, and evaporated. The residue was dissolved in 20 ml $CHCl_3$ and evaporated again. The process was repeated two more times in order to remove TFA completely and afforded 0.18 g (95%) gum. This was used directly for immobilization.

Example 17 describes the hydrolysis of the t-butyl ester Q28FI to obtain Q28FIA. Both Q28FI and Q28FIA are luminophore-ionophores according to the invention and can be used as indicators.

Ester hydrolysis of the compounds Q27FI, Q17FI, Q7FI and Q3FI was carried out in an analogous manner to yield the compounds Q27FIA, Q17FIA, Q7FIA and Q3FIA.

EXAMPLE 18

Immobilization of N-{Bis(4-methylbenzo[5,6,17,18] (O,N,N',O')-]-1,7,16-triaza-cryptand[3,2,2]-2-methoxyethoxy-phenylethylamino]-1',8',-naphthalimidylmethy}benzoic acid (TNBA) on aminocellulose 0.18 g (0.23 mmol) of the indicator Q28FIA, 0.46 g (2.3 mmol) N,N-dicyclohexyl-1,3-carbodiimide, 0.26 g (2.3 mmol) N-hydroxysuccinimide and 5 g (~1.5 meq.) activated cellulose (prepared according to SU 1,028,677, CA 99:177723h) were suspended in 25 ml DMF for 20 h. The cellulose fiber was filtered and washed with 5×50 ml DMF. The fiber was suspended in 25 ml DMF containing 2.85 g (15 mmol) toluenesulfonyl chloride and 1.55 g (15 mmol) TEA. The suspension was stirred at RT for 18 h. The fiber was filtered, washed with 5×50 ml DMF, 50 ml water, 2×50 ml 0.2 N HCl, 50 ml water, 2×50 ml acetone, 2×50 ml ether, and dried at RT for 18 h. This fiber was ready for foil preparation.

Example 18 describes the covalent binding of Q28FIA to aminocellulose. Binding of the compounds Q27FIA, Q17FIA, Q7FIA and Q3FIA to aminocellulose was carried out in an analogous manner.

EXAMPLE 19

Luminescence properties of the triaza-cryptand Q28FIA of the invention immobilized on aminocellulose.

Optical sensors (sensor discs) of the invention were prepared in the following manner:

0.5 g sieved (25 μm) cellulose powder with immobilized indicator prepared according to Example 18 was suspended in 9.5 g 10% hydrogel D4 (Tyndale Plains-Hunter LTD. Ringoes, N.J. 08551) in 90% ethanol-water for 16 h. The resultant homogeneous dispersion was coated onto a polyester foil (Melinex foil, ICI America) at a final dry thickness of 10 μm. This foil was overcoated with 3% carbon black in 10% D4 hydrogel in 90% ethanol-water at a dry thickness of 5 μm. Then a small disc of 2,5 cm diameter was punched out and soaked in buffer for at least 17 h for activation.

Methods of cutting and measuring sensor discs were described by M. J. P. Leiner and P. Hartmann in Sensors and Actuators B, 11 (1993), 281–189 ("Theory and Practice in optical pH sensing") and by M. J. P. Leiner in Analytica Chimica Acta 255 (1991) 209–222.

Figure 5:
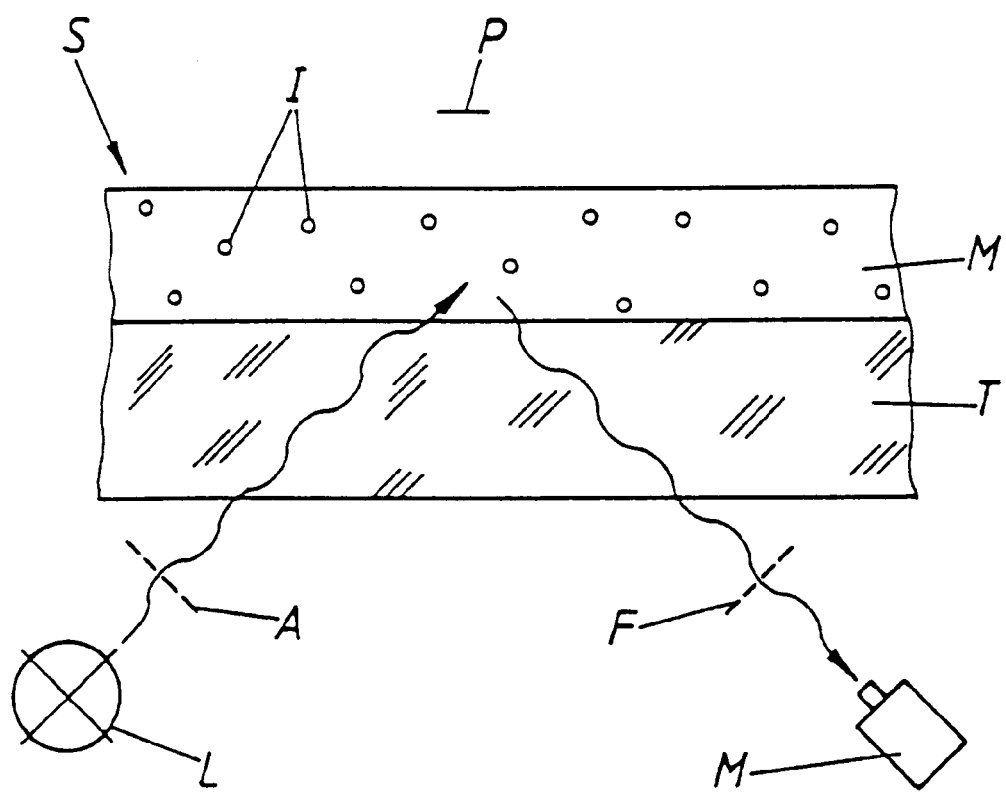
FIG. 5 is a schematic illustration of a luminescence measuring system in accordance with the invention.

The sensor discs thus obtained were used in the measuring set-up represented schematically in FIG. 5.

In FIG. 5, the reference character S denotes a portion of the sensor disc. The compound of the invention suspended in the hydrophilic ion-permeable polymer (hydrogel) and immobilized on aminocellulose is denoted by I. This layer M is carried by a substrate T permeable to excitation and measuring radiation, which is a transparent material.

According to the invention, the compound of the invention I may be bound to the ion-permeable matrix directly in a covalent manner or it may be present in the matrix or in the sample in a physically dissolved condition.

For measurement, the sensor disc was introduced into a thermostatted through-flow cell impervious to light and was contacted with samples P having different concentrations of alkali ions.

The optical measuring system consisted of a blue LED as the light source L, a photodiode M as the detector, optical filters A and F for selecting the wavelengths, a fiber-optic arrangement for conducting the excitation light into the polymer M and the emission light to the photodetector M as well as a device for electronic signal processing (not illustrated). At the excitation end an interference filter (peak transmission at 480 mn), and at the emission end a 520 nm cut-off filter were used.

Figure 10A:
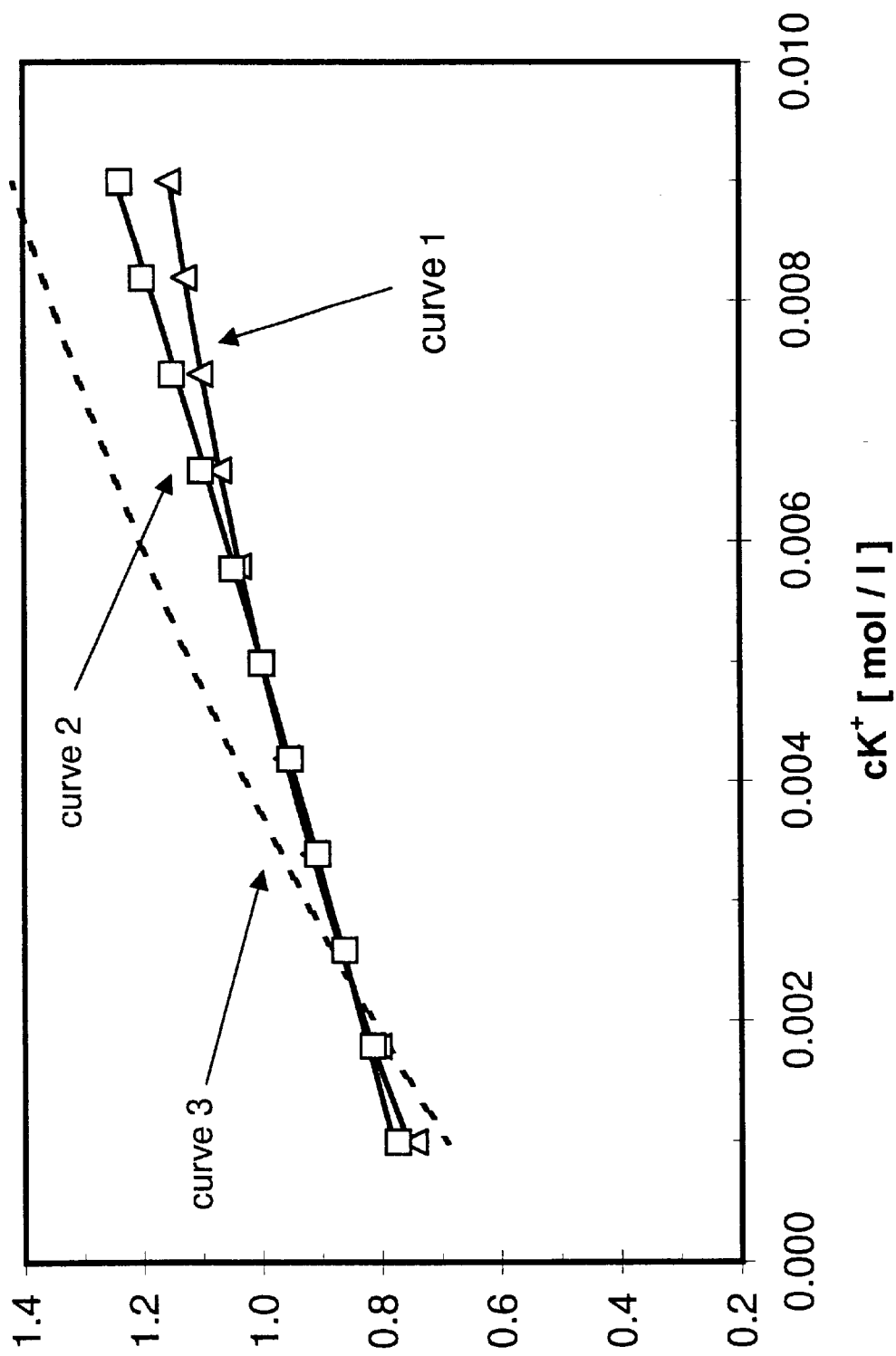
FIG. 10a is a graph illustrating the relative luminescence intensity (ordinate) of a Q28FIA triaza-cryptand in accordance with the invention, immobilized on aminocellulose, as a function of various concentrations of potassium and sodium ions.

FIG. 10a shows the relative luminescence intensity (ordinate) of Q28FIA of the invention, immobilized on aminocellulose, as a function of various concentrations of potassium and sodium ions (Curve 1: $K^+/Na^+$; mmol/l; 1.0/104, 1.8/112, 2.6/121, 3.4/129, 4.2/138, 5.0/146, 5.8/154, 6.6/163, 7.4/171, 8.2/180, 9.0/188); curve 2: $K^+/Na^+$; mmol/l; 1.0/196, 1.8/186, 2.6/176, 3.4/166, 4.2/156, 5.0/146, 5.8/136, 6.6/126, 7.4/116, 8.2/106, 9.0/96). The measuring media used were 0.1 M HEPES buffers, $CO_2$-free, pH 7.396 (37° C.). Curve 3 is the calculated luminescence intensity as a function of the concentration of potassium and in the abscence of sodium ion.

Figure 10B:
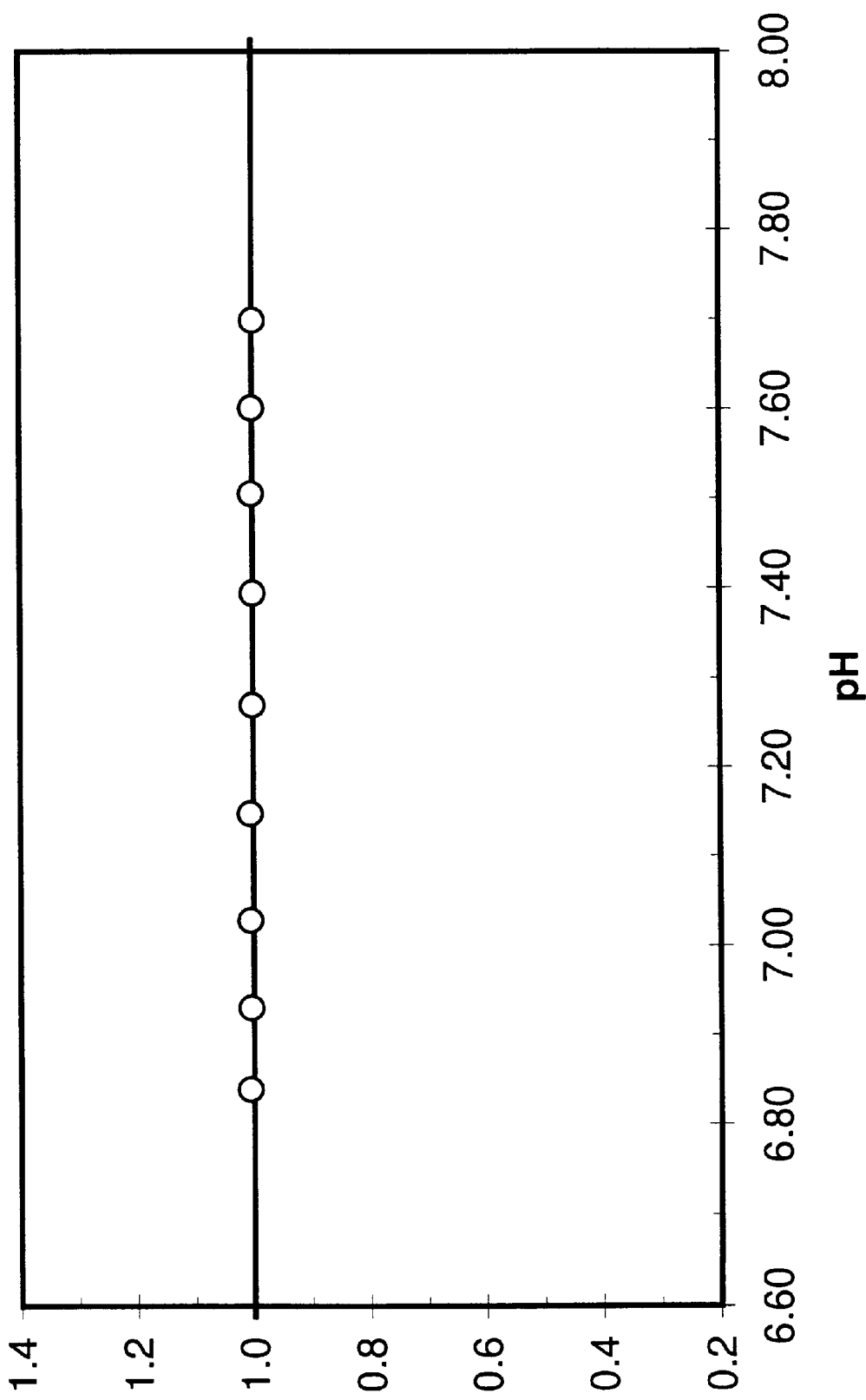
FIG. 10b is a graph illustrating the relative luminescence intensity (ordinate) of a Q28FIA triaza-cryptand in accordance with the invention, immobilized on aminocellulose, as a function of the pH.

FIG. 10b shows the relative luminescence intensity (ordinate) of Q28FIA of the invention, immobilized on aminocellulose as a function of the pH (6.841, 6.932, 7.030, 7.149, 7.271, 7.396, 7.507, 7.603, 7.700). The measuring media used were 0.1 M HEPES buffers with different concentrations of HEPES acid and HEPES-Na salt, 5 mmol/l potassium ion and 146 mmol/l sodium ion.

Figure 10C:
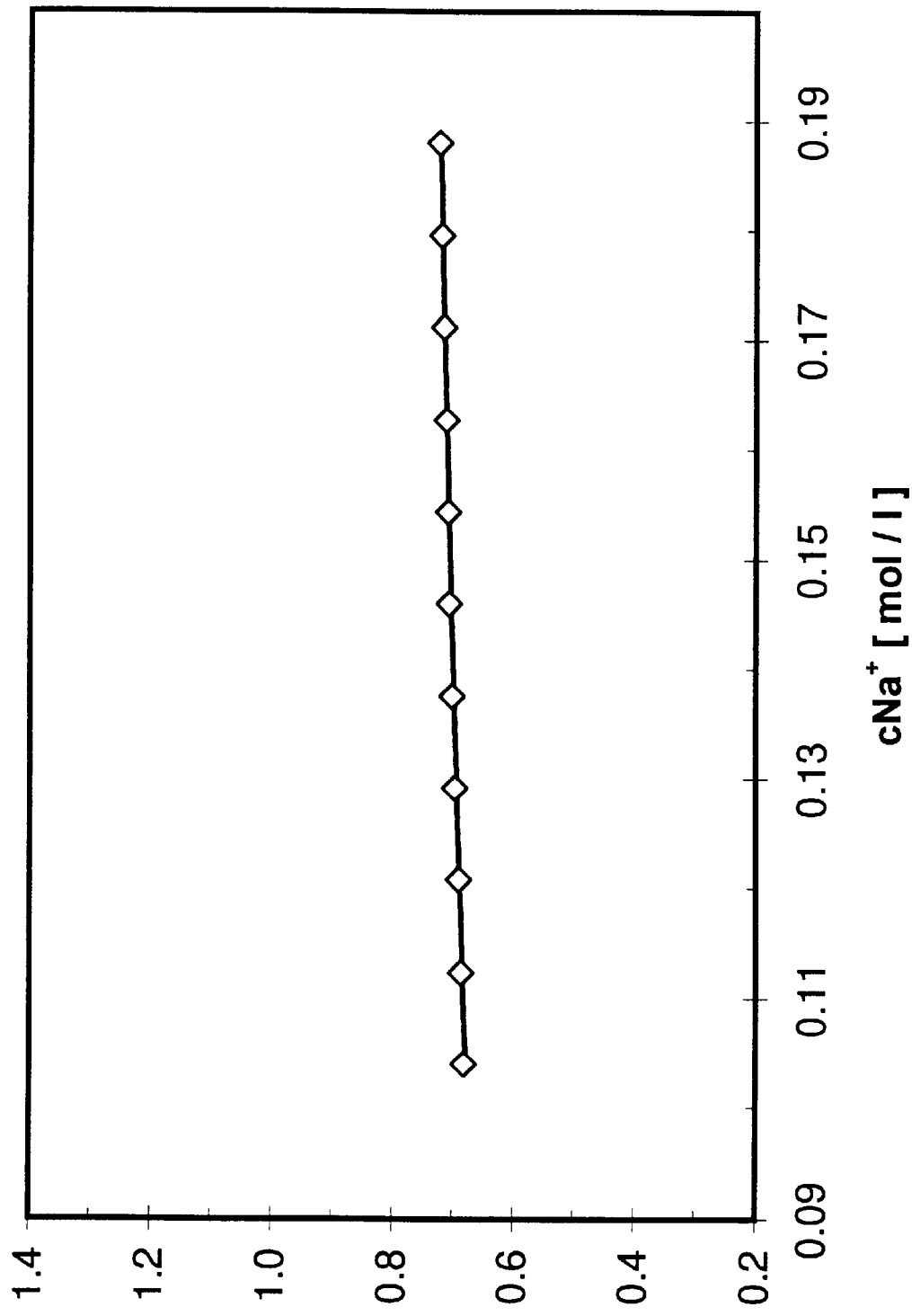
FIG. 10c is a graph illustrating the relative luminescence intensity (ordinate) of a Q28FIA triaza-cryptand in accor-

FIG. 10c shows the relative luminescence intensity (ordinate) of Q28FIA of the invention, immobilized on aminocellulose as a function of various concentrations of sodium ions ($Na^+$; mmol/l; 104, 112, 121, 129, 138, 146, 154, 163, 171, 180, 188). The measuring media used were 0.1 M HEPES buffers, potassium-free, CO2-free, pH 7.396 (37° C.).

It can be seen from FIG. 10c, curves 1 and 2, that within the range 1–9 mmol/l $K^+$, the relative luminescence intensity of Q28FIA depends strongly on $K^+$ with slopes (% signal change) ranging from 3.25–9.5%/mmol/l $K^+$. From curves 1 and 2 it can also be seen that, within the range of 1–9 mmol/l $K^+$, the luminescence intensity depends weakly on variations of $Na^+$ levels within the range of 100–200 mmol/l. From FIG. 10c it can be seen that the latter is also true in the abscence of $K^+$.

EXAMPLE 20

Luminescence properties of the triaza-cryptand Q27FIA of the invention immobilized on aminocellulose Preparation and measurements of the sensor discs were performed according to Example 19.

Figure 9A:
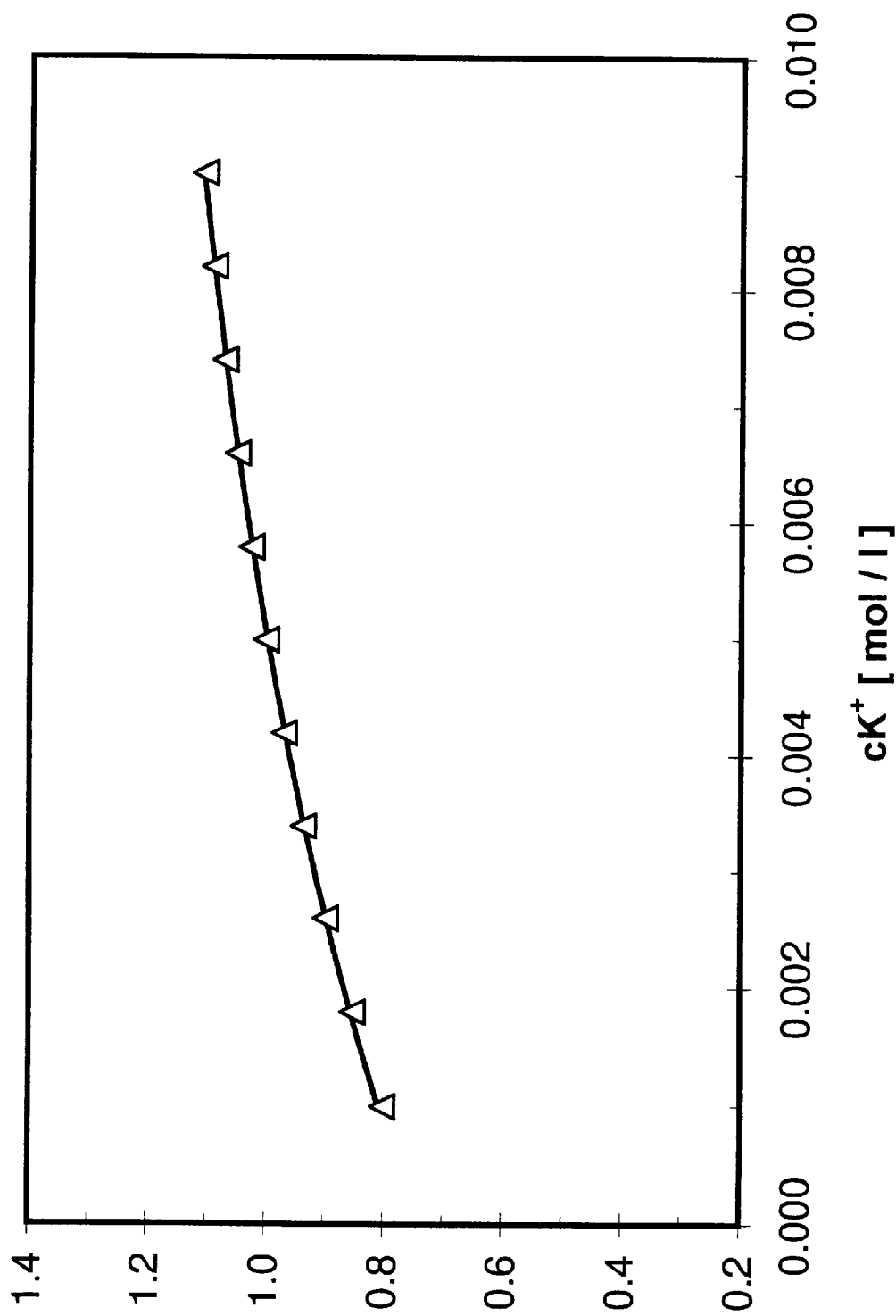
FIG. 9a is a graph illustrating the relative luminescence intensity (ordinate) of a Q27FIA triaza-cryptand in accordance with the invention, immobilized on aminocellulose, as a function of various concentrations of potassium and sodium ions.

FIG. 9a shows the relative luminescence intensity (ordinate) of Q27FIA of the invention, immobilized on aminocellulose, as a function of various concentrations of potassium and sodium ions ($K^+/Na^+$; mmol/l; 1.0/104, 1.8/112, 2.6/121, 3.4/129, 4.2/138, 5.0/146, 5.8/154, 6.6/163, 7.4/171, 8.2/180, 9.0/188). The measuring media used were 0.1 M HEPES buffers, $CO_2$-free, pH 7.396 (37° C.). Curve 3 is the calculated luminescence intensity as a function of the concentration of potassium and in the abscence of sodium ion.

Figure 9B:
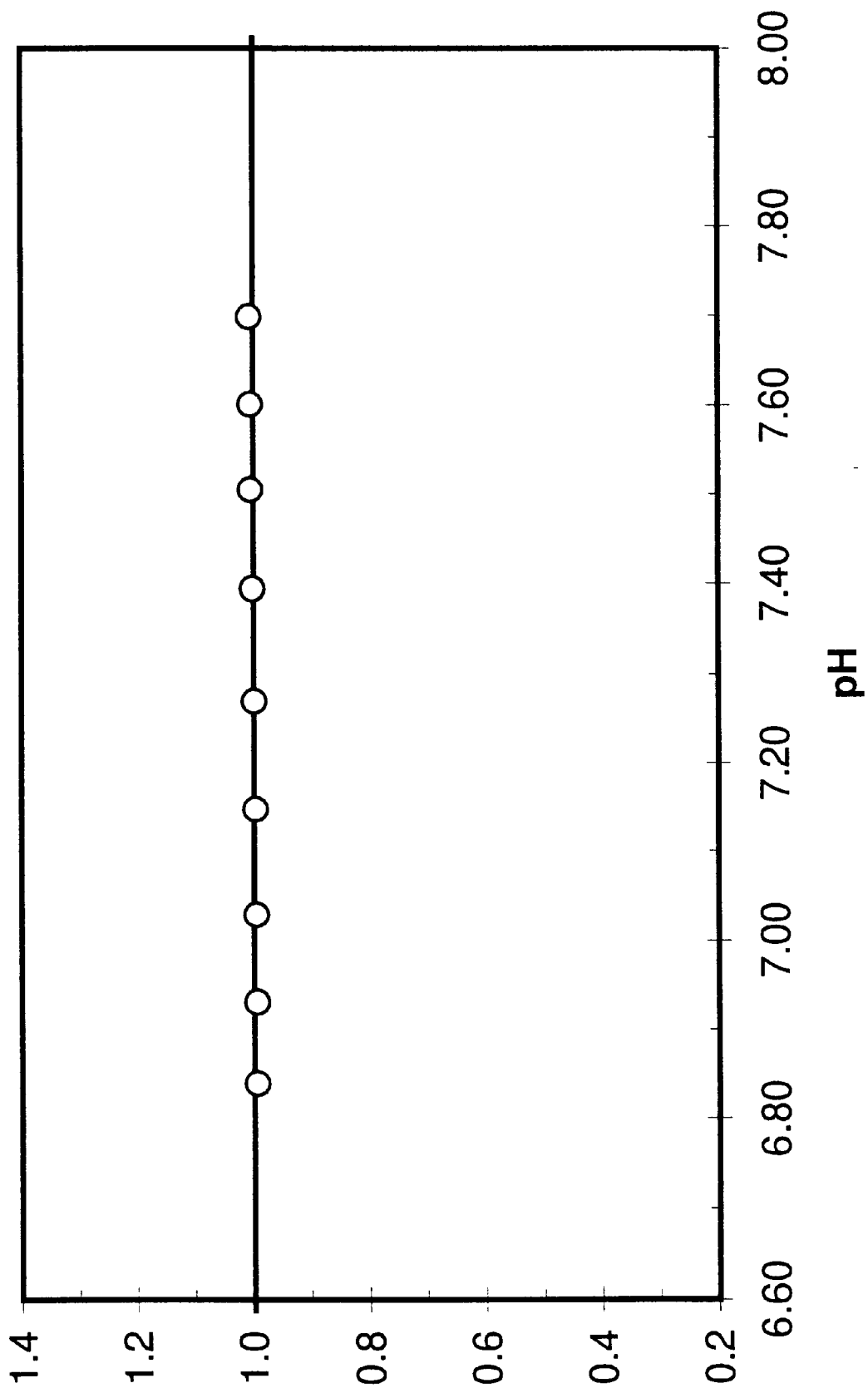
FIG. 9b is a graph illustrating the relative luminescence intensity (ordinate) of a Q27FIA triaza-cryptand in accordance with the invention, immobilized on aminocellulose, as a function of the pH.

FIG. 9b shows the relative luminescence intensity (ordinate) of Q27FIA of the invention, immobilized on aminocellulose, as a function of the pH, determined by using the same media as in FIG. 10b.

Figure 9C:
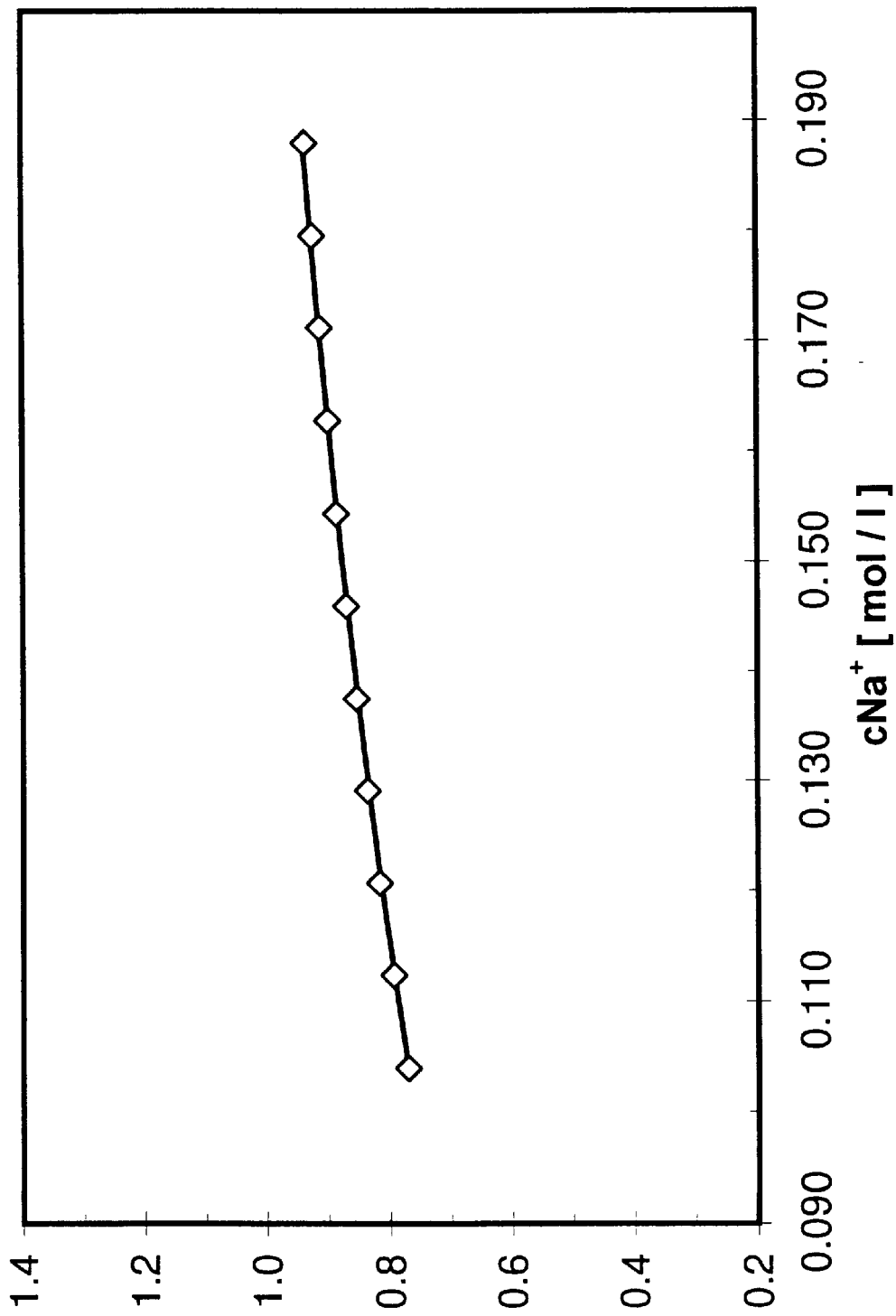
FIG. 9c is a graph illustrating the relative luminescence intensity (ordinate) of a Q27FIA triaza-cryptand in accordance with the invention, immobilized on aminocellulose, as a function of various concentrations of sodium ions.

FIG. 9c shows the relative luminescence intensity (ordinate) of Q27FIA of the invention, immobilized on amino-cellulose, as a function of various concentrations of sodium ions, determined by using the same media as in FIG. 10c.

EXAMPLE 21

Luminescence properties of the triaza-cryptand Q17FIA of the invention immobilized on aminocellulose Preparation and measurements of the sensor discs were performed according to Example 19.

Figure 8A:
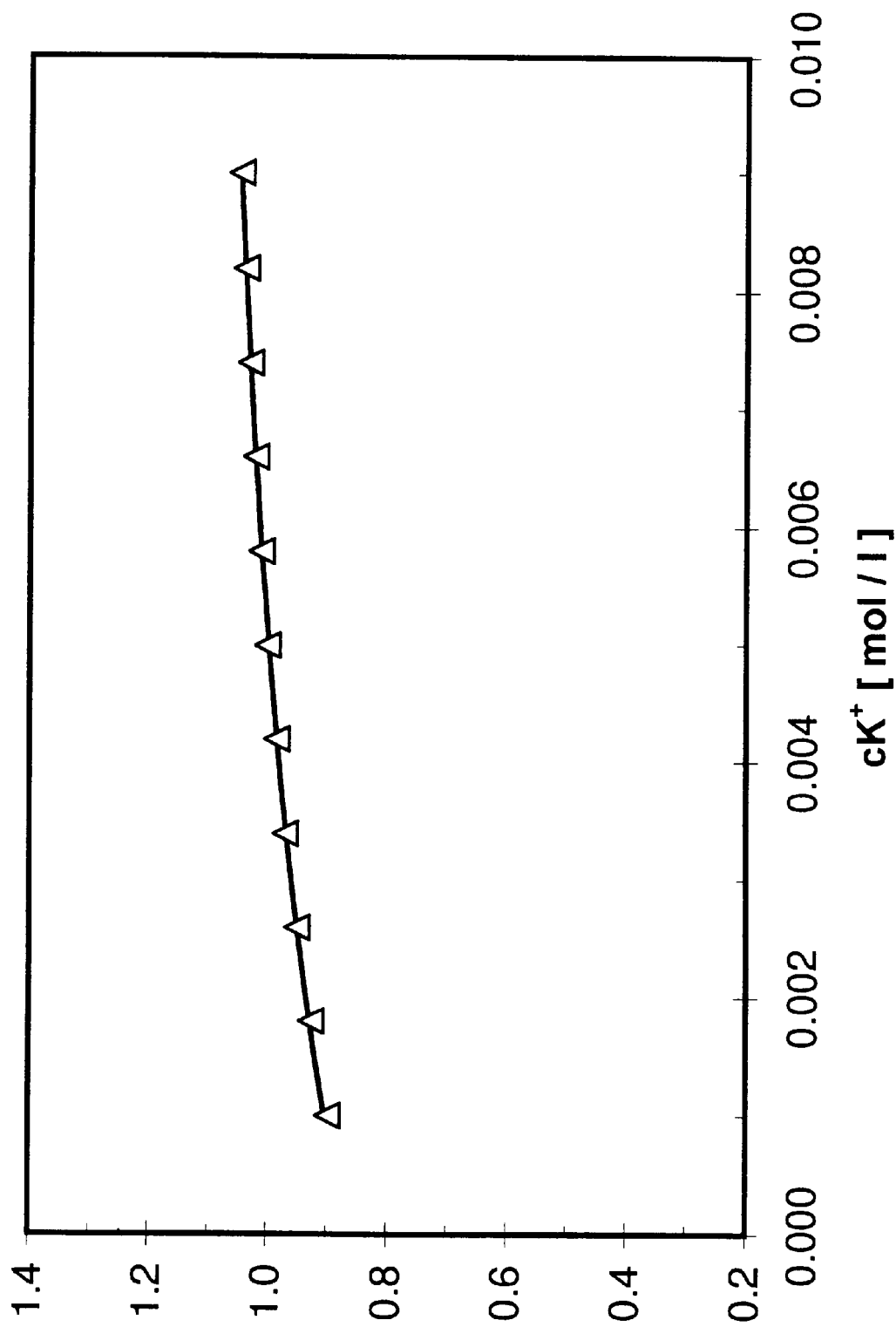
FIG. 8a is a graph illustrating the relative luminescence intensity (ordinate) of a Q17FIA triaza-cryptand in accordance with the invention, immobilized on aminocellulose, as a function of various concentrations of potassium and sodium ions.

FIG. 8a shows the relative luminescence intensity (ordinate) of Q17FIA of the invention, immobilized on aminocellulose, as a function of various concentrations of potassium and sodium ions, determined by using the same media as in FIG. 9a.

Figure 8B:
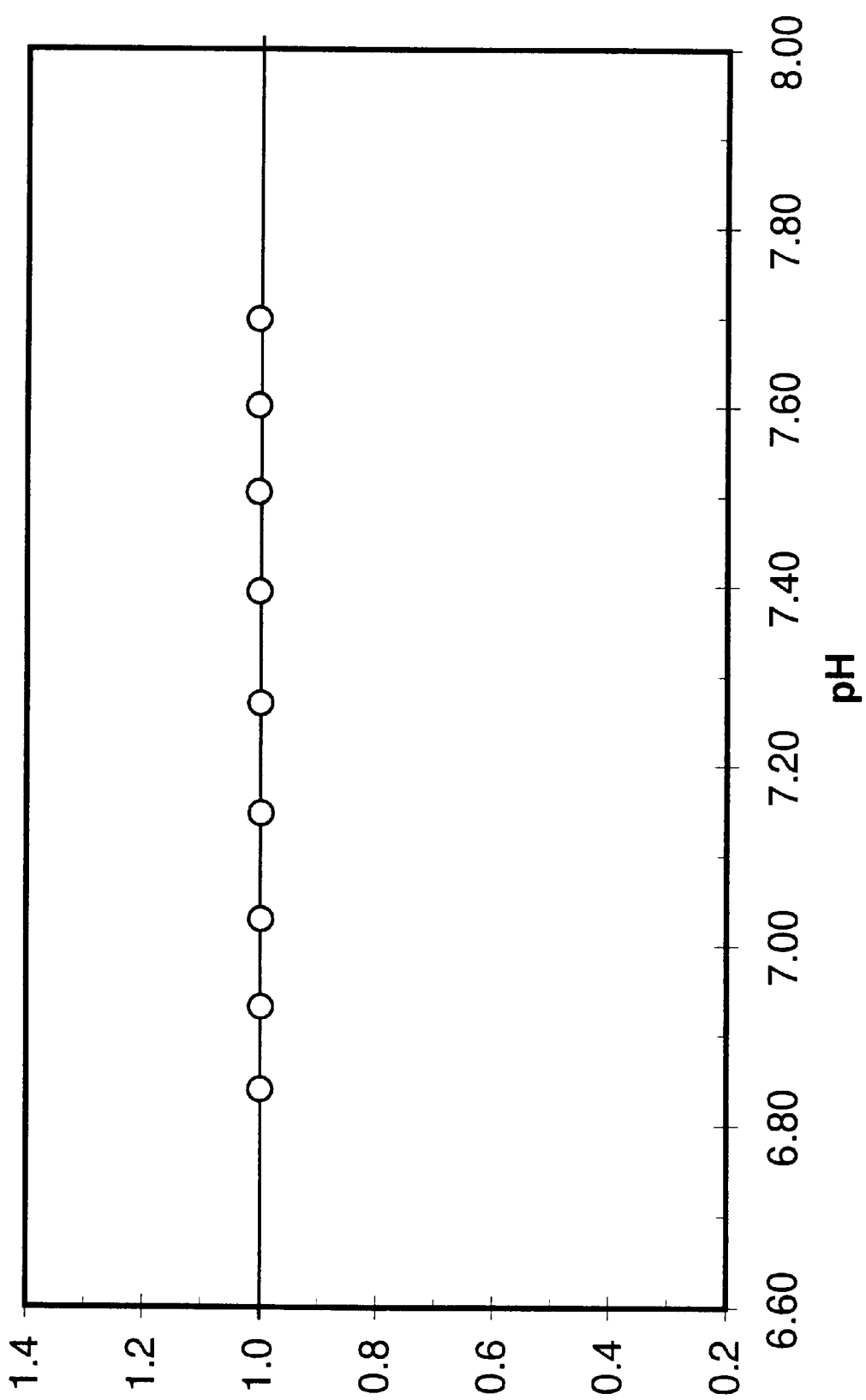
FIG. 8b is a graph illustrating the relative luminescence intensity (ordinate) of a Q17FIA triaza-cryptand in accordance with the invention, immobilized on aminocellulose, as a function of the pH.

FIG. 8b shows the relative luminescence intensity (ordinate) of Q17FIA of the invention, immobilized on amino-cellulose, as a function of the pH, determined by using the same media as in FIG. 10b.

Figure 8C:
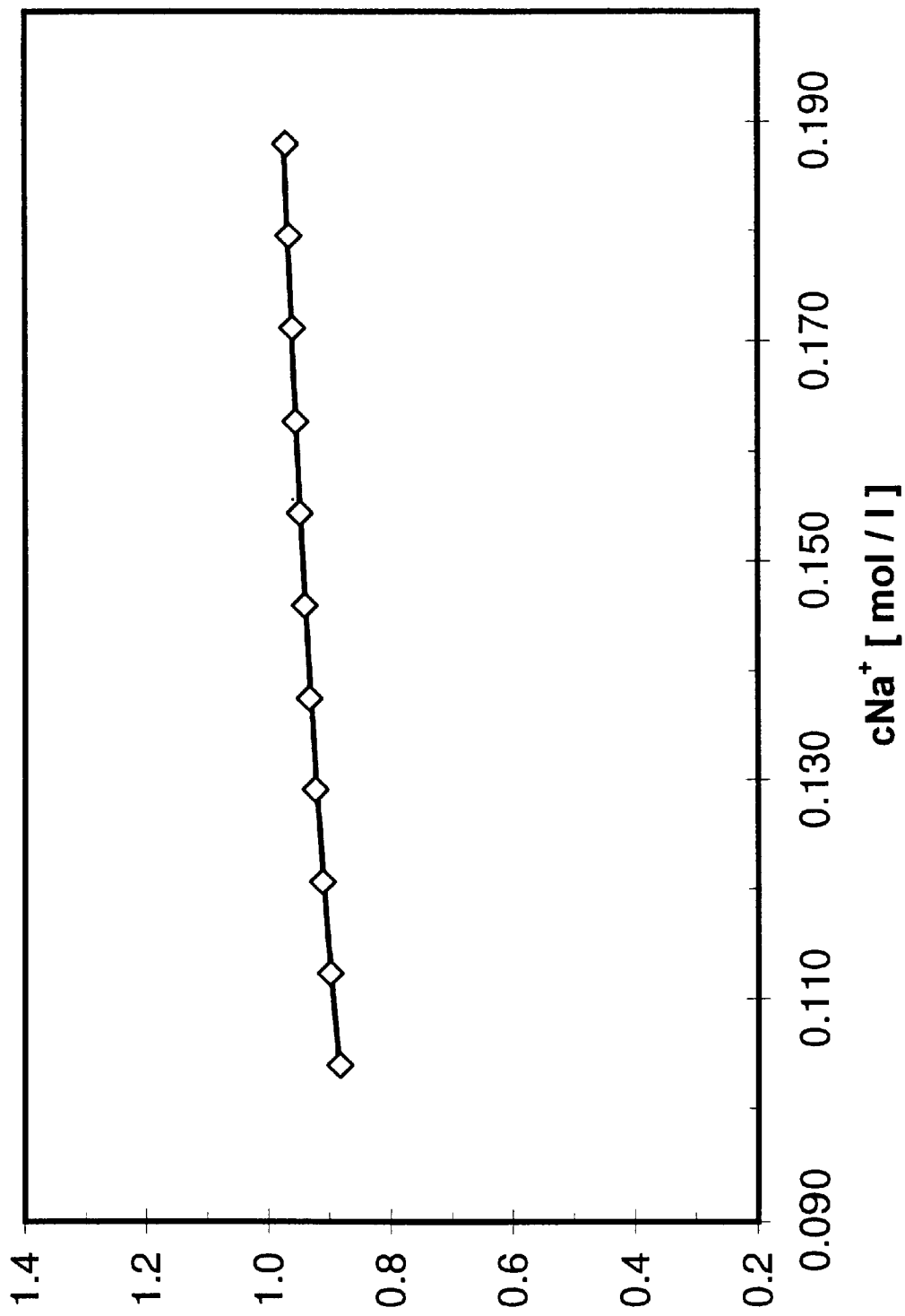
FIG. 8c is a graph illustrating the relative luminescence intensity (ordinate) of a Q17FIA triaza-cryptand in accordance with the invention, immobilized on aminocellulose, as a function of various concentrations of sodium ions.

FIG. 8c shows the relative luminescence intensity (ordinate) of Q17FIA of the invention, immobilized on aminocellulose, as a function of various concentrations of sodium ions, determined by using the same media as in FIG. 10c.

EXAMPLE 22

Luminescence properties of the triaza-cryptand Q7FIA of the invention immobilized on aminocellulose Preparation and measurements of the sensor discs were performed according to Example 19.

Figure 7A:
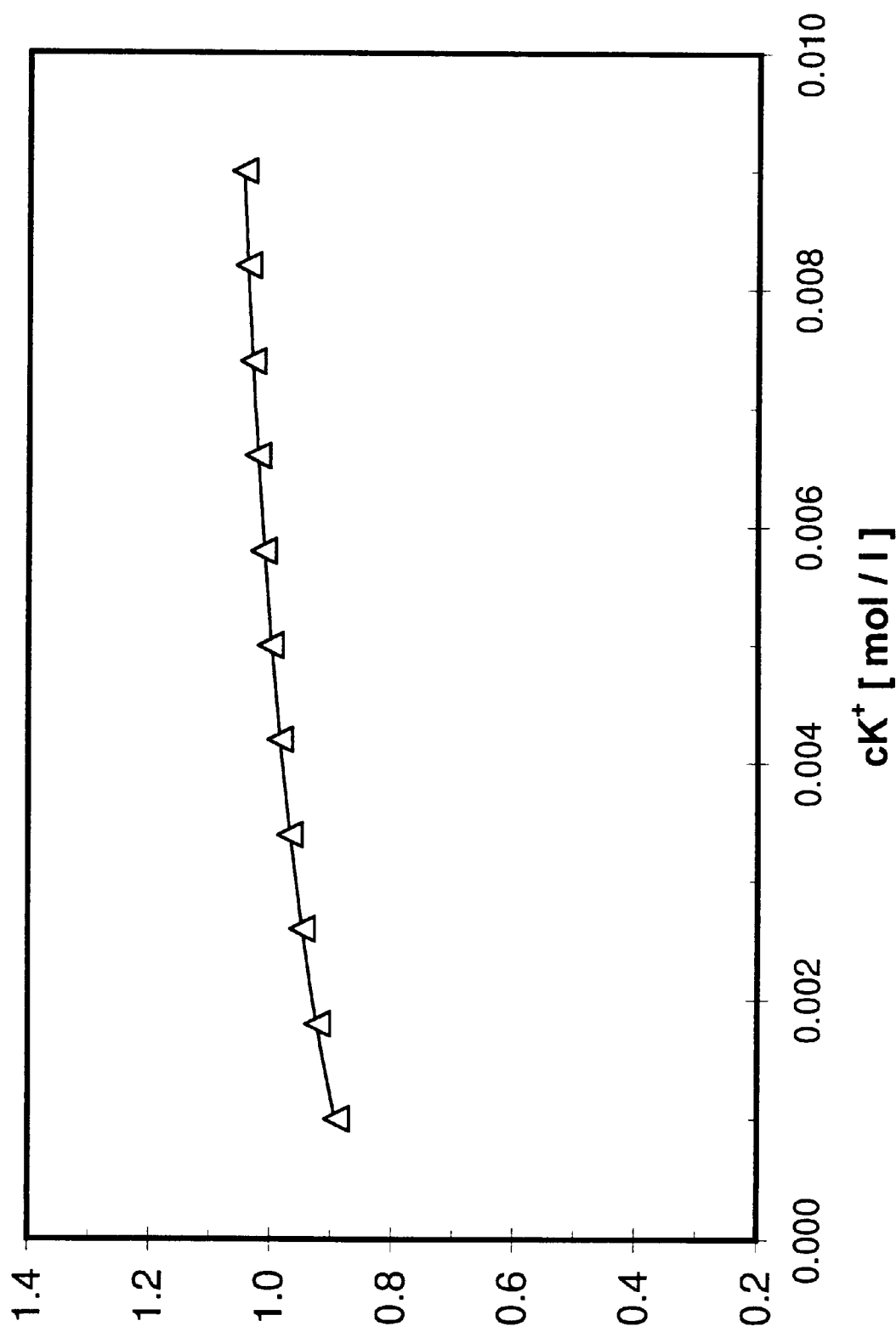
FIG. 7a is a graph illustrating the relative luminescence intensity (ordinate) of a Q7FIA triaza-cryptand in accordance with the invention, immobilized on aminocellulose, as a function of various concentrations of potassium and sodium ions.

FIG. 7a shows the relative luminescence intensity (ordinate) of Q7FIA of the invention, immobilized on aminocellulose, as a function of various concentrations of potassium and sodium ions, determined by using the same media as in FIG. 9a.

Figure 7B:
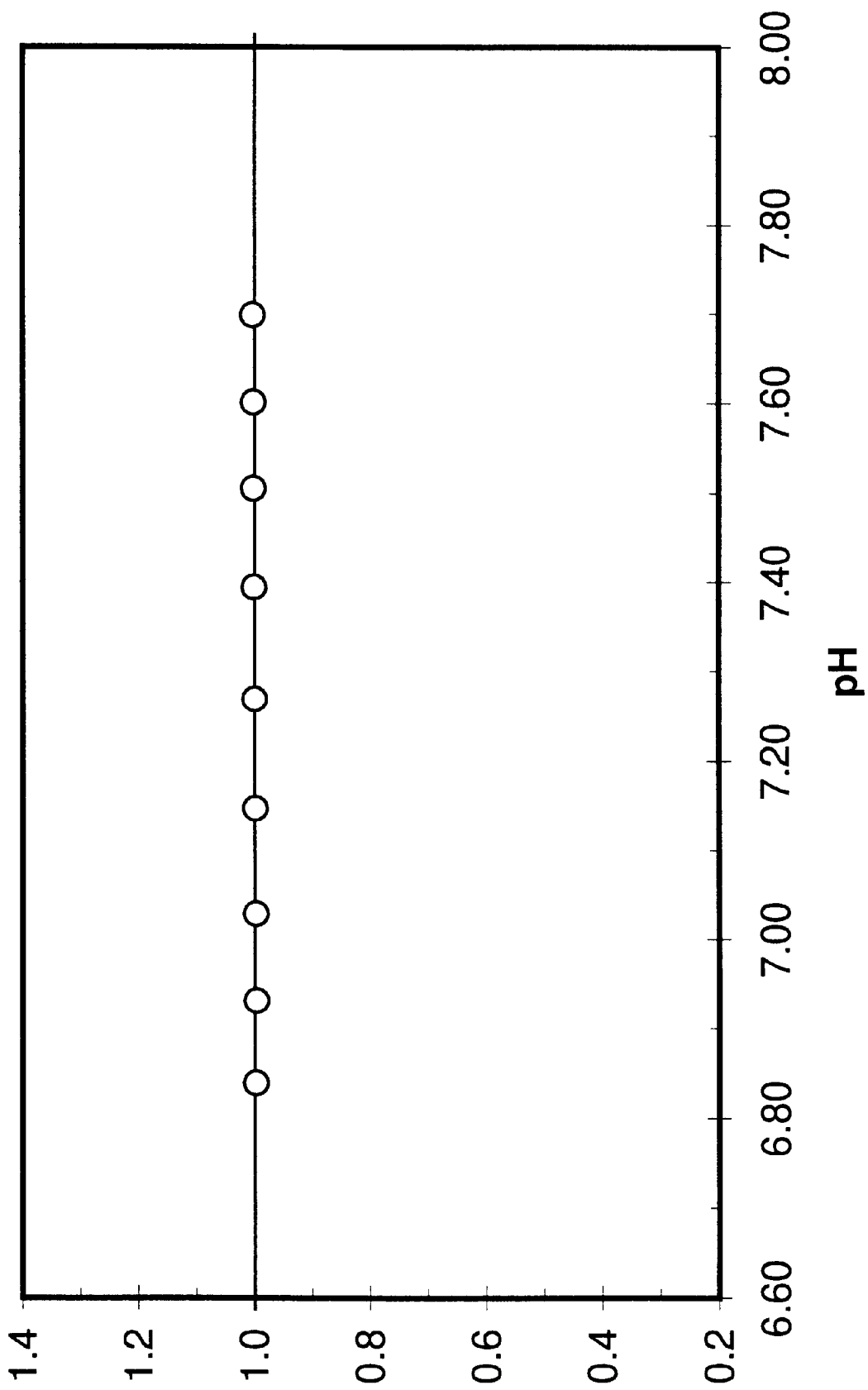
FIG. 7b is a graph illustrating the relative luminescence intensity (ordinate) of a Q7FIA triaza-cryptand in accordance with the invention, immobilized on aminocellulose, as a function of the pH.

FIG. 7b shows the relative luminescence intensity (ordinate) of Q7FIA of the invention, immobilized on amino-cellulose, as a function of the pH, determined by using the same media as in FIG. 10b.

Figure 7C:
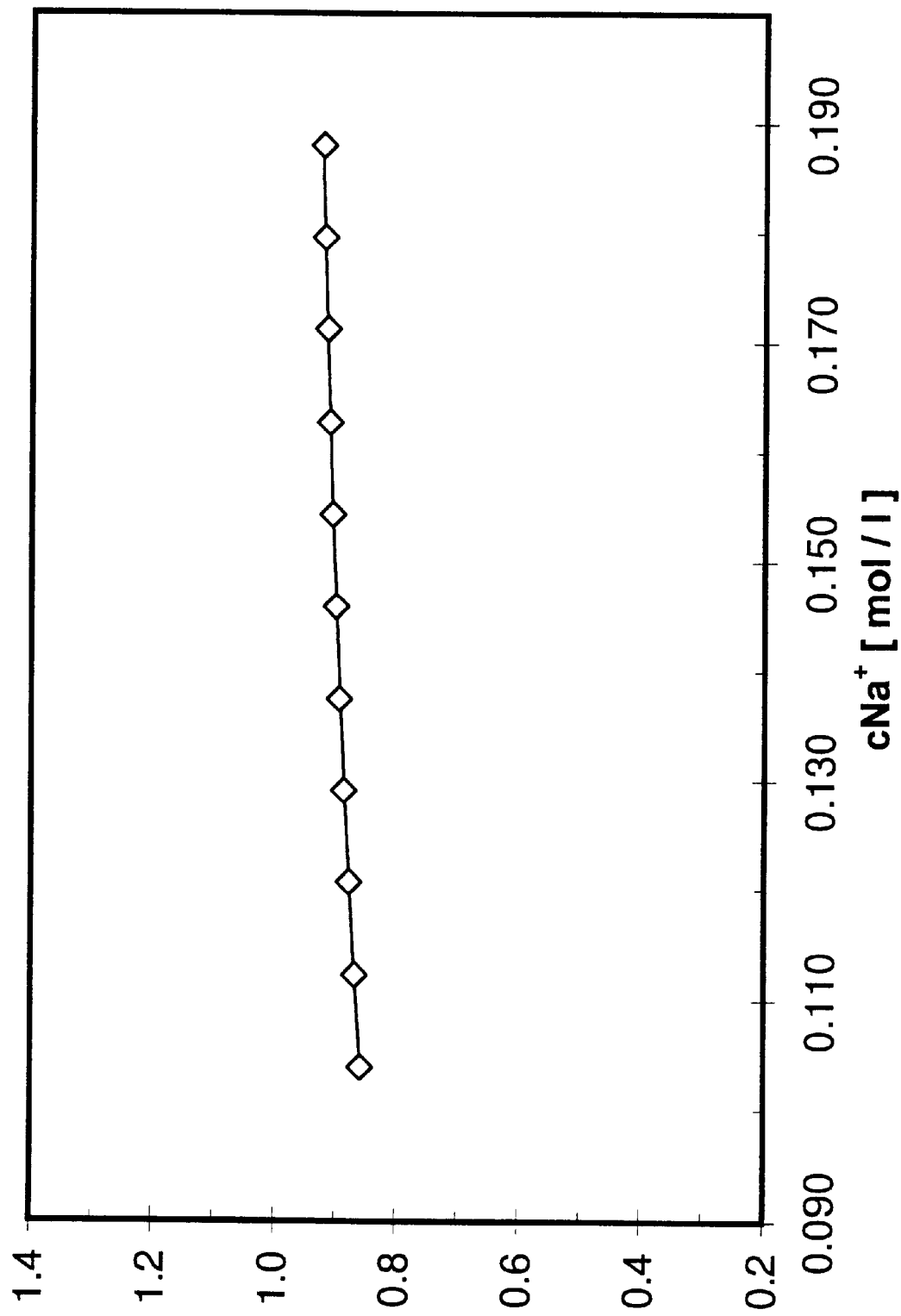
FIG. 7c is a graph illustrating the relative luminescence intensity (ordinate) of a Q7FIA triaza-cryptand in accordance with the invention, immobilized on aminocellulose, as a function of various concentrations of sodium ions.

FIG. 7c shows the relative luminescence intensity (ordinate) of Q7FIA of the invention, immobilized on aminocellulose, as a function of various concentrations of sodium ions, determined by using the same media as in FIG. 10c.

As can be seen from FIGS. 10b, 9b, 8b, 7b luminophore-ionophores according to the invention with two aryl-bound bridging nitrogen atoms are insensitive to physiological pH values. This is also true (not shown) for basic values of pH.

EXAMPLE 23

Calculation of sensor specific parameters for the sensors according to the invention used in Examples 19 to 22

Table 1 shows the sensor specific parameters $Kd_K$, $Kd_{Na}$, qo and q(Na) for the indicators Q28FIA, Q27FIA, Q7FIA and Q17FIA immobilized on aminocellulose.

TABLE 1

| Indicator | $Kd_K$ | $Kd_{Na}$ | qo | q(Na) |
| --- | --- | --- | --- | --- |
| Q28FIA | 0.0176 | 0.142 | 0.18 | 0.27 |
| Q27FIA | 0.0130 | 0.102 | 0.10 | 0.75 |
| Q7FIA | 0.0024 | 0.024 | 0.10 | 0.77 |
| Q17FIA | 0.0056 | 0.033 | 0.10 | 0.83 |

Table 2a, 2b, 2c and 2d show the signal changes [%/(mmol/l)] at different concentrations of $K^+$ and $Na^+$ for the indicators Q28FIA, Q27FIA, Q7FIA and Q17FIA, respectively. The values were calculated by fitting the measured data shown in FIGS. 7 to 10 to Equation 6 by means of commercially available least square algorithms.

TABLE 2a

Q28FIA

| | | slope | |
| --- | --- | --- | --- |
| $cK^+$ mmol/l | $cNa^+$ mmol/l | $K^+$ %/(mmol/l) | $Na^+$ %/(mmol/l) |
| 0.1 | 145 | 9.50 | 0.28 |
| 1 | 145 | 8.34 | 0.14 |
| 5 | 145 | 5.21 | −0.18 |
| 10 | 145 | 3.35 | −0.34 |
| 0,1 | 0 | 25.5 | — |
| 1 | 0 | 18.9 | — |
| 5 | 0 | 7.9 | — |
| 10 | 0 | 4.0 | — |
| 0 | 0.1 | — | 1.5 |
| 0 | 1 | — | 1.5 |
| 0 | 10 | — | 1.3 |
| 0 | 100 | — | 0.4 |

TABLE 2b

Q27FIA

| | | slope | |
| --- | --- | --- | --- |
| $cK^+$ mmol/l | $cNa^+$ mmol/l | $K^+$ %/(mmol/l) | $Na^+$ %/(mmol/l) |
| 0.1 | 145 | 3.42 | 0.89 |
| 1 | 145 | 3.14 | 0.80 |
| 5 | 145 | 2.24 | 0.50 |
| 10 | 145 | 1.58 | 0.29 |
| 0.1 | 0 | 63.7 | — |
| 1 | 0 | 36.3 | — |
| 5 | 0 | 10.3 | — |
| 10 | 0 | 4.5 | — |
| 0 | 0.1 | — | 25.0 |
| 0 | 1 | — | 23.3 |
| 0 | 10 | — | 13.3 |
| 0 | 100 | — | 1.5 |

TABLE 2c

Q7FIA

| | | slope | |
| --- | --- | --- | --- |
| $cK^+$ mmol/l | $cNa^+$ mmol/l | $K^+$ %/(mmol/l) | $Na^+$ %/(mmol/l) |
| 0.1 | 145 | 2.83 | 0.33 |
| 1 | 145 | 2.49 | 0.25 |
| 5 | 145 | 1.53 | 0.05 |
| 10 | 145 | 0.95 | −0.05 |
| 0.1 | 0 | 267.7 | — |
| 1 | 0 | 52.3 | — |
| 5 | 0 | 5.5 | — |
| 10 | 0 | 1.7 | — |
| 0 | 0.1 | — | 107.9 |
| 0 | 1 | — | 81.3 |
| 0 | 10 | — | 18.8 |
| 0 | 100 | — | 0.7 |

TABLE 2d

Q17FIA

| | | slope | |
| --- | --- | --- | --- |
| $cK^+$ mmol/l | $cNa^+$ mmol/l | $K^+$ %/(mmol/l) | $Na^+$ %/(mmol/l) |
| 0.1 | 145 | 1.45 | 0.43 |
| 1 | 145 | 1.35 | 0.38 |
| 5 | 145 | 1.01 | 0.24 |
| 10 | 145 | 0.74 | 0.13 |
| 0.1 | 0 | 135.7 | — |
| 1 | 0 | 49.3 | — |
| 5 | 0 | 8.6 | — |
| 10 | 0 | 3.1 | — |
| 0 | 0.1 | — | 86.6 |
| 0 | 1 | — | 68.9 |
| 0 | 10 | — | 19.3 |
| 0 | 100 | — | 0.8 |

The data shown in Table 1 indicate, for instance, for Q28FIA that the free luminophore-ionophore (L) has 17% of the intensity of the $K^+$ saturated ionophore ($LK^+$) and $LNa^+$ has 27% of the intensity compared to $LK^+$.

Q7, Q17 and Q27 have smaller cavities for ion binding as compared to Q28. Compared to Q28, the smaller cavity of Q27 increases the ability to bind $Na^+$ (as supported by the lower Kd value) and increases the ability of $Na^+$ to inhibit the PET effect, as supported by the higher $qNa^+$ value.

A further decrease of the cavity size will yield an ionophore (i.e., Q18) with a higher selectivity for $Na^+$ than for $K^+$ (i.e., lower Kd for $Na^+$ than for $K^+$) and, therefore, suitable for the determination of $Na^+$.

Q17, Q7, Q27 have the same cavity size for ion binding. Q27 differs from Q17 and Q7 with respect to the length of the ether chain in the 2-position of the non-bridging nitrogen. A comparison of the Kd values in Table 1 indicates that varying the length of the chain (i.e. methoxy vs. methoxyethoxy) can be used as a further tool to adjust the Kd values.

EXAMPLE 24

Luminescence properties of the triaza-cryptand Q3FIA of the invention immobilized on aminocellulose Preparation and measurements of the sensor discs were performed according to Example 19.

Figure 6A:
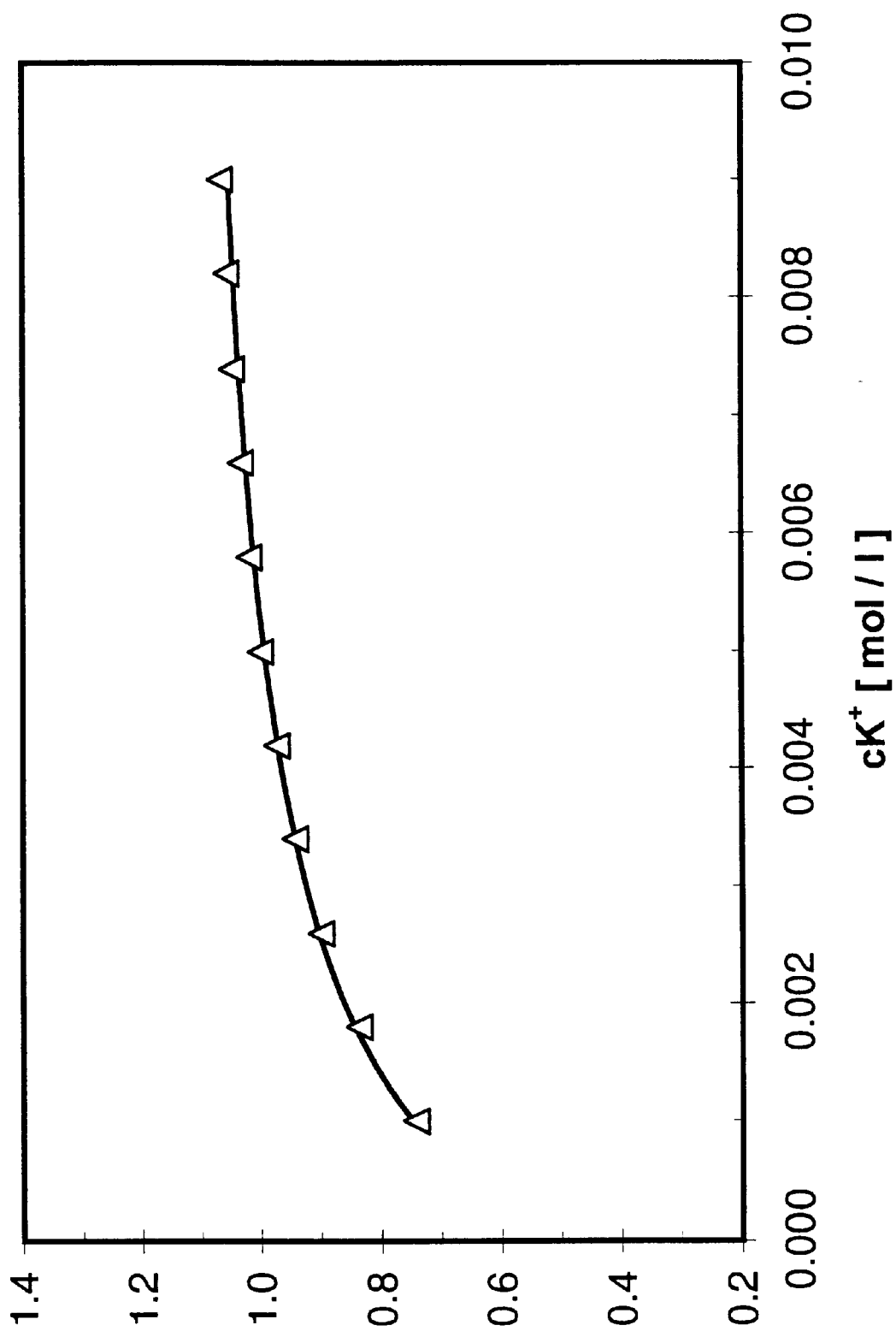
FIG. 6a is a graph illustrating the relative luminescence intensity (ordinate) of a Q3FIA triaza-cryptand in accordance with the invention, immobilized on aminocellulose, as a function of various concentrations of potassium and sodium ions.

FIG. 6a shows the relative luminescence intensity (ordinate) of Q3FIA of the invention, immobilized on aminocellulose, as a function of various concentrations of potassium and sodium ions, determined by using the same media as in FIG. 9a.

Figure 6B:
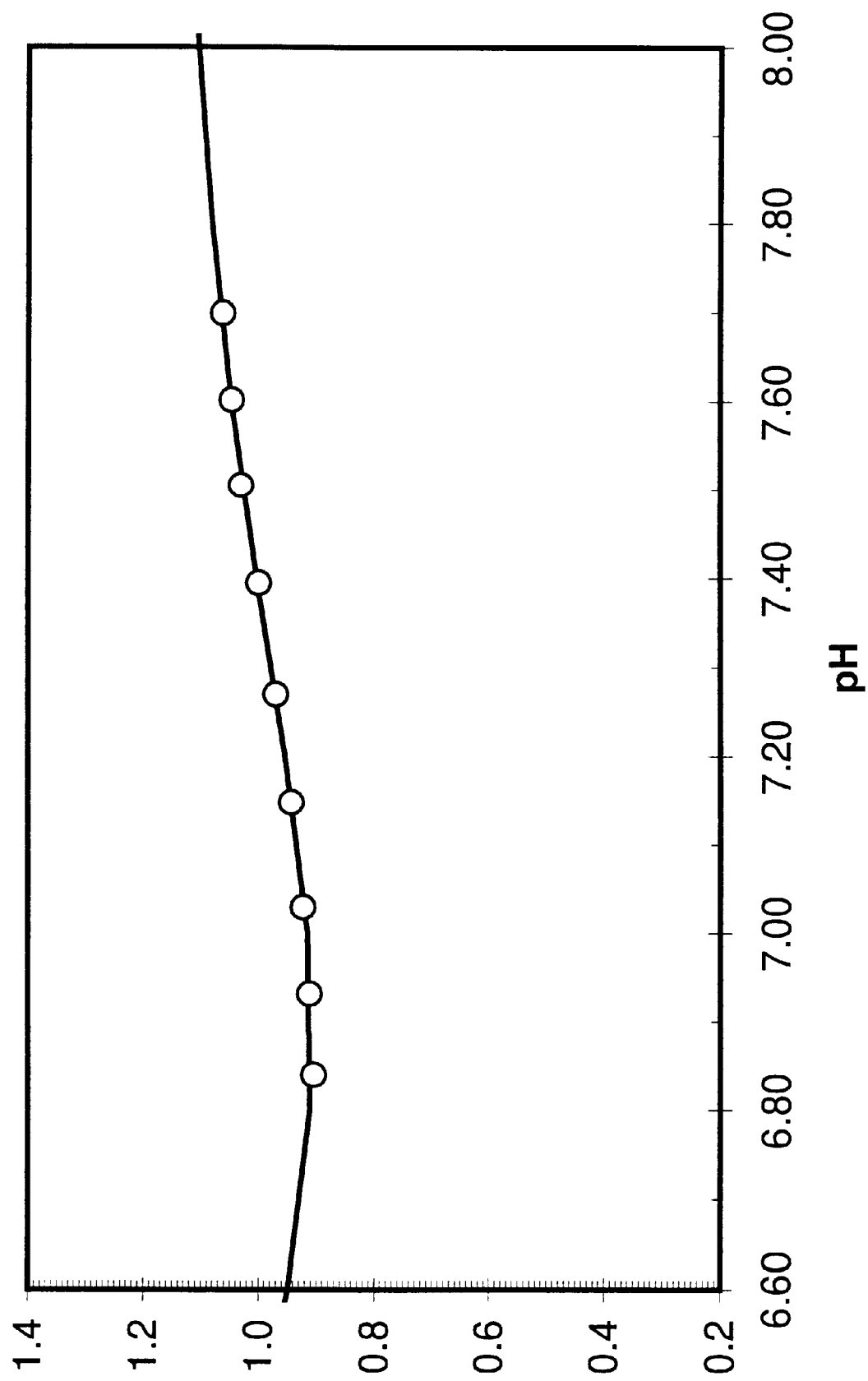
FIG. 6b is a graph illustrating the relative luminescence intensity (ordinate) of a Q3FIA triaza-cryptand in accordance with the invention, immobilized on aminocellulose, as a function of the pH.

FIG. 6b shows the relative luminescence intensity (ordinate) of Q3FIA of the invention, immobilized on aminocellulose, as a function of the pH, determined by using the same media as in FIG. 10b.

Figure 6C:
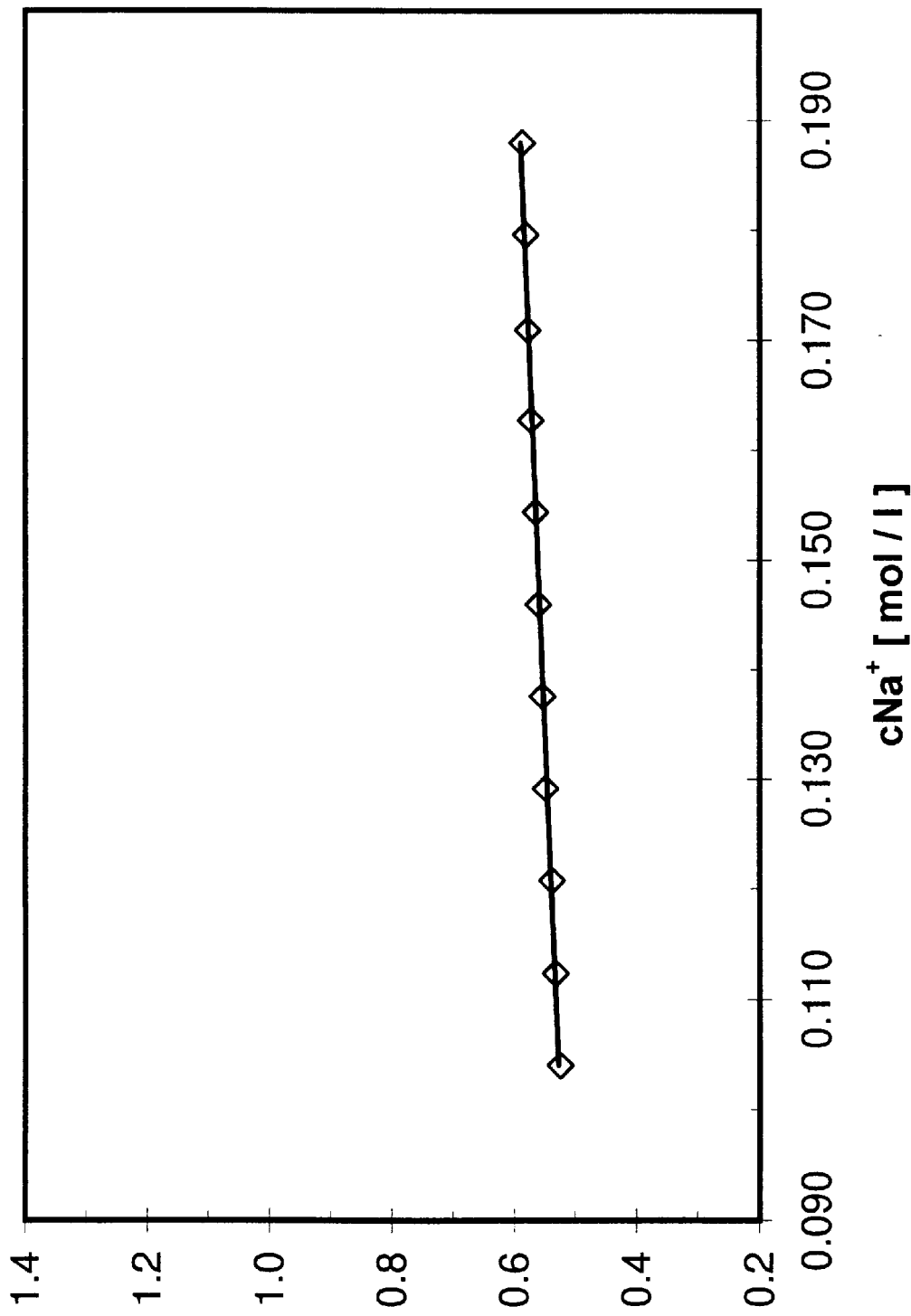
FIG. 6c is a graph illustrating the relative luminescence intensity (ordinate) of a Q3FIA triaza-cryptand in accordance with the invention, immobilized on aminocellulose, as a function of various concentrations of sodium ions.

FIG. 6c shows the relative luminescence intensity (ordinate) of Q3FIA of the invention, immobilized on aminocellulose, as a function of various concentrations of sodium ions, determined by using the same media as in FIG. 10c.

As can be seen from FIG. 6b, in the neutral pH range, the luminescence intensity of Q3FIA depends on the pH. Due to the two aliphatic bridging nitrogens Q3 can reversibly bind protons at neutral and weakly basic pH values with pK values of approximately 7.0 and 9.7, respectively. The pK values show that Q3FIA will be pH insensitive at strongly basic pH values. Protons can be considered as interfering cations and, therefore, the effects of pH may be corrected via Equations 6 and 7.

The example demonstrates that triaza-cryptands with two aliphatic bridging nitrogen atoms according to the invention can be used for the determination of cations, preferably for media with high pH values (i.e., above 11), or for pH neutral and weakly pH buffered media. Correction for pH is possible, but less preferable.

Similar is true for the triaza-cryptands with one aliphatic and one aromatic bound bridging nitrogen atom according to the invention. The pK value of the aliphatic nitrogen atom can be expected to be between 7 and 9.

We claim:

1. A triaza-cryptand of the general Formula I

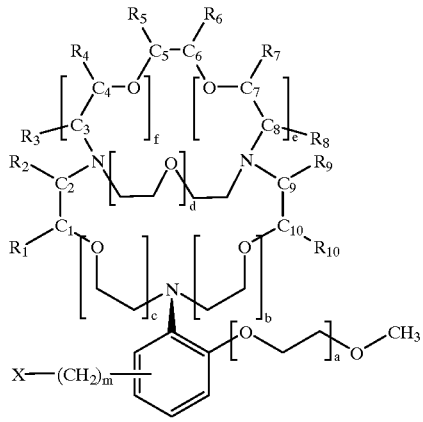

(I)

wherein a is selected from the group consisting of 0 and 1, b and c independently are selected from the group consisting of 0 and 1, with the proviso that not both of b and c are 0, d is selected from the group consisting of 1, 2 and 3, e and f independently are selected from the group consisting of 0 and 1, with the proviso that not both of e and f are 0, $R_1$ and $R_2$ are either hydrogen or form an alkyl($C_1$–$C_4$) benzene ring or an alkoxy($C_1$–$C_4$) benzene ring together with $C_1$ and $C_2$, wherein $C_2$ is the para position, $R_3$ and $R_4$ are either hydrogen or form an alkyl($C_1$–$C_4$) benzene ring or an alkoxy($C_1$–$C_4$) benzene ring together with $C_3$ and $C_4$, wherein $C_3$ is the para position, $R_5$ and $R_6$ are either hydrogen or form a benzene ring or a naphtalene ring together with $C_5$ and $C_6$, $R_7$ and $R_8$ are either hydrogen or form an alkyl($C_1$–$C_4$) benzene ring or an alkoxy($C_1$–$C_4$) benzene ring together with $C_7$ and $C_8$, wherein $C_8$ is the para position, $R_9$ and $R_{10}$ are either hydrogen or form an alkyl($C_1$–$C_4$) benzene ring or an alkoxy($C_1$–$C_4$) benzene ring together with $C_9$ and $C_{10}$, wherein $C_9$ is the para position, X is a luminophoric moiety in ortho, para or meta position with respect to the nitrogen and m is selected from the group consisting of 0, 1 and 2.

2. A triaza-cryptand according to claim 1, wherein the luminophoric moiety X is selected from the group consisting of an aminonaphthalimide group having the general Formula II

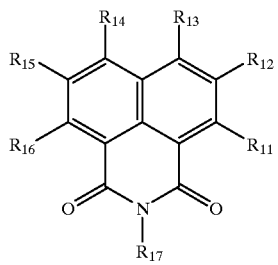

(II)

wherein at least one of $R_{11}$, $R_{12}$, $R_{13}$, $R_{14}$, $R_{15}$ and $R_{16}$ is an —NH-group through which X is bound to the group —$(CH_2)_m$— and the remaining groups and $R_{17}$ independently are selected from the group consisting of hydrogen, a lipophilic group, a hydrophilic group and a reactive group for coupling to a polymer, and a xanthenone group having the general formula III

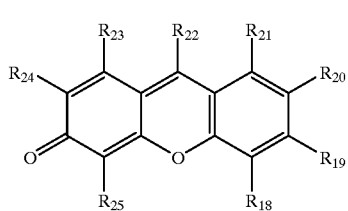

(III)

wherein m=0 and at least one of $R_{18}$, $R_{19}$, $R_{20}$, $R_{21}$, $R_{22}$, $R_{23}$, $R_{24}$, and $R_{25}$ represents a chemical bond through which X is bound directly to the ionophoric moiety and the remaining groups are each selected from the group consisting of —OH, —$OR_{26}$, wherein $R_{26}$ is a hydrophilic or a lipophilic group, —O—$R_{27}$—G, wherein $R_{27}$ is a hydrophilic or a lipophilic group and G is a reactive group for coupling to a polymer, and —$(CH_2)_n$—COOH, wherein n is a number between 0 and 17, and a compound having the general Formula IV

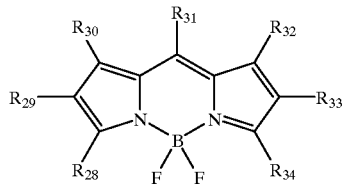

(IV)

wherein at least one of $R_{28}$, $R_{29}$, $R_{30}$, $R_{31}$, $R_{32}$, $R_{33}$ und $R_{34}$ represents a chemical bond through which X is bound to the group —$(CH_2)_m$— and the remaining groups independently are selected from the group consisting of hydrogen, a lipophilic group, a hydrophilic group and a reactive group for coupling to a polymer or a biomolecule, or $R_{29}$ forms an aromatic ring system together with $R_{30}$ and $R_{33}$ forms an aromatic ring system together with $R_{34}$, and a luminescent metal ligand complex.

3. A triaza-cryptand according to claim 1 or 2, wherein each of the three nitrogens of the cryptand is bound to at least one aryl group.

4. A triaza-cryptand according to claim 3, wherein
a=1, b=1, c=1, d=2, e=1, f=1,
$R_3$, $R_4$, $R_5$, $R_6$, $R_7$ and $R_8$ are hydrogen,
$R_1$ and $R_2$ form a toluene ring together with $C_1$ and $C_2$, wherein $C_2$ is the para position, and
$R_9$ and $R_{10}$ form a toluene ring together with $C_9$ and $C_{10}$, wherein $C_9$ is the para position.

5. A triaza-cryptand according to claim 3, wherein
a=0, b=1, c=1, d=1, e=0, f=1,
$R_3$, $R_4$, $R_5$ and $R_6$ are hydrogen,
$R_1$ and $R_2$ form a toluene ring together with $C_1$ and $C_2$, wherein $C_2$ is the para position, and
$R_9$ and $R_{10}$ form a toluene ring together with $C_9$ and $C_{10}$, wherein $C_9$ is the para position.

6. A method of determining an alkali ion in a sample comprising the steps of:
providing a compound having a luminophoric moiety and an ionophoric moiety
reacting the ionophoric moiety with the alkali ion present in the sample, wherein the luminophoric moiety changes its luminescence properties,
measuring the luminescence, and
determining the presence of the alkali ion in the sample utilizing the measured luminescence,
wherein the compound is a triaza-cryptand according to claim 1.

7. A method according to claim 6, wherein the sample has a pH of above 6,5 and the compound is a triaza-cryptand according to claim 3.

8. A method according to claim 6 for determining potassium ions.

9. A method according to claim 8, wherein the compound is a triaza-cryptand according to claim 4.

10. A method according to claim 6 or 7 for determining sodium ions, wherein the compound is a triaza-cryptand according to claim 5.

11. A method according to claim 6, wherein the relative luminescence intensity of the luminophore-ionophore in contact with the ions of the sample is measured and the concentration of the alkali ion is determined utilizing the measured luminescence by a method comprising the steps of
calibrating the luminophore-ionophore in a calibration medium, wherein the relative luminescence intensity $Sm_M$ of the luminophore-ionophore fully saturated with the analyte alkali ion M is determined according to Equation 8 and
determining the concentration cM of the analyte alkali ion M in the sample according to Equation 7.

12. A method according to claim 6, wherein the time-dependent luminescence intensity of the luminophore-ionophore in contact with the ions of the sample is measured after switching off the excitation light and the concentration of the alkali ion is determined utilizing the measured time-dependent luminescence by determining the concentration cM of the analyte alkali ion M in the sample according to Equation 10 and the ratio $A_{LM}/A_L$ is determined according to Equation 9.

13. An optical sensor for determining alkali ions in a sample, which sensor has a matrix comprising a compound having a luminophoric moiety and an ionophoric moiety, wherein the compound is a triaza-cryptand according to claim 1.

* * * * *